(12) United States Patent
Bettinger et al.

(10) Patent No.: US 9,333,273 B2
(45) Date of Patent: *May 10, 2016

(54) TARGETING CONSTRUCTS

(71) Applicant: BRACCO SUISSE S.A., Manno (CH)

(72) Inventors: Thierry Bettinger, Peillonnex (FR); Philippe Bussat, Pers-Jussy (FR); Samir Cherkaoui, Feigeres (FR); Irene Guilbert-Brigger, Divonne les Bains (FR); Bernard Lamy, Saint-Julien-en-Genevois (FR)

(73) Assignee: BRACCO SUISSE S.A., Manno (CH)

( * ) Notice: Subject to any disclaimer, the term of this patent is extended or adjusted under 35 U.S.C. 154(b) by 0 days.

This patent is subject to a terminal disclaimer.

(21) Appl. No.: 14/927,865

(22) Filed: Oct. 30, 2015

(65) Prior Publication Data

US 2016/0074539 A1 Mar. 17, 2016

Related U.S. Application Data

(63) Continuation of application No. 13/814,329, filed as application No. PCT/EP2011/063720 on Aug. 9, 2011, now Pat. No. 9,211,348.

(30) Foreign Application Priority Data

Aug. 9, 2010 (EP) .................... 10172318

(51) Int. Cl.
*A61K 49/22* (2006.01)
*A61K 38/17* (2006.01)

(52) U.S. Cl.
CPC .............. *A61K 49/223* (2013.01); *A61K 49/222* (2013.01); *A61K 49/227* (2013.01); *A61K 38/178* (2013.01)

(58) Field of Classification Search
None
See application file for complete search history.

(56) References Cited

U.S. PATENT DOCUMENTS

| | | | |
|---|---|---|---|
| 4,276,885 | A | 7/1981 | Tickner et al. |
| 5,271,928 | A | 12/1993 | Schneider et al. |
| 5,413,774 | A | 5/1995 | Schneider et al. |
| 5,445,813 | A | 8/1995 | Schneider et al. |
| 5,556,610 | A | 9/1996 | Yan et al. |
| 5,597,549 | A | 1/1997 | Schneider et al. |
| 5,605,673 | A | 2/1997 | Schutt et al. |
| 5,711,933 | A | 1/1998 | Bichon et al. |
| 5,827,504 | A | 10/1998 | Yan et al. |
| 5,840,679 | A | 11/1998 | Larsen et al. |
| 6,333,021 | B1 | 12/2001 | Schneider et al. |
| 2003/0166521 | A1 | 9/2003 | Eppihimer |
| 2006/0241022 | A1 | 10/2006 | Bowen |
| 2010/0196284 | A1 | 8/2010 | Lindner et al. |

FOREIGN PATENT DOCUMENTS

| | | |
|---|---|---|
| CN | 101374955 A | 2/2009 |
| EP | 0324938 A1 | 7/1989 |
| EP | 0554213 A1 | 8/1993 |
| JP | 2003-529610 A | 10/2003 |
| JP | 2010-524969 A | 7/2010 |
| WO | 91-15244 A2 | 10/1991 |
| WO | 94-09829 A1 | 5/1994 |
| WO | 97-29782 A1 | 8/1997 |
| WO | 2004-069284 A2 | 8/2004 |
| WO | 2007-067979 A2 | 6/2007 |
| WO | 2008-131217 A1 | 10/2008 |
| WO | 2009-074569 A1 | 6/2009 |

OTHER PUBLICATIONS

Cummings, R.D., "Structure and function of selectin ligang PSGL-1", Brazilian Journal of Medical and Biological Research, 1999, vol. 32, No. 5, pp. 519-528, ISSN 0100-879X.

Hermanson, Greg T., "Bioconjugate Techniques", Elsevier, 2nd Ed., 2008, Chapter 1, Section 4.1: Introduction of Sulfhydryl Residues (Thiolation), pp. 67-101.

Ju Tongzhong et al., "Purification, Characterization and Subunit Structure of Rat Core 1 β 1,3-Galactosyltransferase", The Journal of Biological Chemistry (J. Biol. Chem.), 2002, vol. 277, pp. 169-177, Doi:10.1074, original online publicaiton Oct. 22, 2001.

Leppanen, Anne et al.: "A novel glycosulfopeptide binds to P-selectin and inhibits leukocyte adhesion to P-selectin", Journal of Biological Chemistry, American Society for Biochemistry adn Molecular Biology, INC, US, vol. 274, No. 35, Aug. 27, 1999, pp. 24838-24848, XP002176950, ISSN: 0021-9258.

Liu Wen-jun et al: "Identification of N-terminal residues on P-selectin glycoprotein ligand-1 required for binding to P-selectin", Journal of Biological Chemistry, American Society for Biochemistry and Molecular Biology, INC., US, vol. 273, No. 12, Mar. 20, 1998, pp. 7078-7087, XP002116309, ISSN: 0021-9258.

Mulder, William J. M. et al: "Lipid-based nanoparticles for contrast-enhanced MRI", NMR in Biomedicine, vol. 19, pp. 142-164, Jan. 1, 2006, Wiley, London, GB, XP008091928, ISSN: 0952-3480.

Rychak, J. J. et al: "Selectin ligands promote ultrasound contrast agent adhesion under shear flow", Molecular Pharmaceutics, vol. 3, No. 5, Oct. 2006, pp. 516-524, XP002612674, ISSN: 1543-8384.

Office Action for Australian application No. 2011288511, mail date Dec. 11, 2014 [B0591/064 AU].

Office Action for Chinese application No. 201180039277.X, mail date Apr. 30, 2014 (English translation) [B0591/064 CN].

Office Action for Chinese application No. 201180039277.X, mail date Jan. 20, 2015 (English translation) [B0591/064 CN].

(Continued)

*Primary Examiner* — Lianko Garyu

(74) *Attorney, Agent, or Firm* — Vivicar Law, PLLC

(57) ABSTRACT

Gas-filled microvesicles associated with a polypeptide comprising a sequence of amino acids, said sequence exhibiting binding affinity for selectins, particularly p-selectin. The gas-filled microvesicles can be used in ultrasound imaging.

27 Claims, No Drawings

(56) References Cited

OTHER PUBLICATIONS

First Office Action for Japanese application No. 2013-523598, mail date Oct. 21, 2014 (with English Office Action Summary as provided by agent) [B0591/064 JP].
European Search Report for European application No. 10172318.7, mail date Dec. 14, 2010 [B0591/064 EP-P0].
PCT international Search Report for PCT/EP2011/063720, mail date Jan. 2, 2012 [B0591/064 WO].
PCT Written Opinion for PCT/EP2011/063720, mail date Jan. 2, 2012 [B0591/064 WO].
PCT International Preliminary Report on Patentability/Written Opinion for PCT/EP2011/063270, mail date Feb. 21, 2013 [B0591/064 WO].

```
                        SEQUENCE LISTING

<160> NUMBER OF SEQ ID NOS: 4

<210> SEQ ID NO 1
<211> LENGTH: 47
<212> TYPE: PRT
<213> ORGANISM: Homo sapiens
<220> FEATURE:
<221> NAME/KEY: DOMAIN
<222> LOCATION: (1)..(47)
<223> OTHER INFORMATION: NH2 term mature P-selectin glycoprotein
      ligand-1 (GenBank Acc. NO: Q14242) (fragment aa 42-88).

<400> SEQUENCE: 1

Gln Ala Thr Glu Tyr Glu Tyr Leu Asp Tyr Asp Phe Leu Pro Glu Thr
1               5                   10                  15

Glu Pro Pro Glu Met Leu Arg Asn Ser Thr Asp Thr Thr Pro Leu Thr
            20                  25                  30

Gly Pro Gly Thr Pro Glu Ser Thr Thr Val Glu Pro Ala Ala Arg
        35                  40                  45

<210> SEQ ID NO 2
<211> LENGTH: 24
<212> TYPE: PRT
<213> ORGANISM: Artificial
<220> FEATURE:
<223> OTHER INFORMATION: spacer
<220> FEATURE:
<221> NAME/KEY: MISC_FEATURE
<222> LOCATION: (1)..(24)
<223> OTHER INFORMATION: spacer: N-terminal fragment of Fc Human IgG
      region

<400> SEQUENCE: 2

Pro His Thr Cys Pro Pro Cys Pro Ala Pro Glu Ala Leu Gly Ala Pro
1               5                   10                  15

Ser Val Phe Leu Phe Pro Pro Lys
            20

<210> SEQ ID NO 3
<211> LENGTH: 71
<212> TYPE: PRT
<213> ORGANISM: artificial
<220> FEATURE:
<223> OTHER INFORMATION: fusion protein (SEQIDNO:1 + SEQIDNO:2)
<220> FEATURE:
```

```
<221> NAME/KEY: MISC_FEATURE
<222> LOCATION: (1)..(71)
<223> OTHER INFORMATION: SEQIDNO:1 + SEQIDNO:2

<400> SEQUENCE: 3

Gln Ala Thr Glu Tyr Glu Tyr Leu Asp Tyr Asp Phe Leu Pro Glu Thr
1               5                   10                  15

Glu Pro Pro Glu Met Leu Arg Asn Ser Thr Asp Thr Thr Pro Leu Thr
            20                  25                  30

Gly Pro Gly Thr Pro Glu Ser Thr Thr Val Glu Pro Ala Ala Arg Pro
        35                  40                  45

His Thr Cys Pro Pro Cys Pro Ala Pro Glu Ala Leu Gly Ala Pro Ser
 50                  55                  60

Val Phe Leu Phe Pro Pro Lys
 65                  70

<210> SEQ ID NO 4
<211> LENGTH: 272
<212> TYPE: PRT
<213> ORGANISM: Artificial
<220> FEATURE:
<223> OTHER INFORMATION: PSGL-1 Fc region fusion protein
<220> FEATURE:
<221> NAME/KEY: SITE
<222> LOCATION: (1)..(47)
<223> OTHER INFORMATION: P-selectin glycoprotein ligand-1 (PSGL-1), aa
      42-88 GenBank Acc. N0 Q14242.
<220> FEATURE:
<221> NAME/KEY: SITE
<222> LOCATION: (48)..(71)
<223> OTHER INFORMATION: spacer
<220> FEATURE:
<221> NAME/KEY: MISC_FEATURE
<222> LOCATION: (72)..(272)
<223> OTHER INFORMATION: IgG Fc region (from US2003/0166521)

<400> SEQUENCE: 4

Gln Ala Thr Glu Tyr Glu Tyr Leu Asp Tyr Asp Phe Leu Pro Glu Thr
1               5                   10                  15

Glu Pro Pro Glu Met Leu Arg Asn Ser Thr Asp Thr Thr Pro Leu Thr
            20                  25                  30

Gly Pro Gly Thr Pro Glu Ser Thr Thr Val Glu Pro Ala Ala Arg Pro
        35                  40                  45

His Thr Cys Pro Pro Cys Pro Ala Pro Glu Ala Leu Gly Ala Pro Ser
 50                  55                  60

Val Phe Leu Phe Pro Pro Lys Pro Lys Asp Thr Leu Met Ile Ser Arg
 65                  70                  75                  80

Thr Pro Glu Val Thr Cys Val Val Asp Val Ser His Glu Asp Pro
                85                  90                  95

Glu Val Lys Phe Asn Trp Tyr Val Asp Gly Val Glu Val His Asn Ala
                100                 105                 110

Lys Thr Lys Pro Arg Glu Glu Gln Tyr Asn Ser Thr Tyr Arg Val Val
            115                 120                 125

Ser Val Leu Thr Val Leu His Gln Asp Trp Leu Asn Gly Lys Glu Tyr
        130                 135                 140

Lys Cys Lys Val Ser Asn Lys Ala Leu Pro Val Pro Ile Glu Lys Thr
145                 150                 155                 160

Ile Ser Lys Ala Lys Gly Gln Pro Arg Glu Pro Gln Val Tyr Thr Leu
                165                 170                 175

Pro Pro Ser Arg Glu Glu Met Thr Lys Asn Gln Val Ser Leu Thr Cys
            180                 185                 190
```

```
Leu Val Lys Gly Phe Tyr Pro Ser Asp Ile Ala Val Glu Trp Glu Ser
        195                 200                 205

Asn Gly Gln Pro Glu Asn Asn Tyr Lys Thr Thr Pro Pro Val Leu Asp
        210                 215                 220

Ser Asp Gly Ser Phe Phe Leu Tyr Ser Lys Leu Thr Val Asp Lys Ser
225                 230                 235                 240

Arg Trp Gln Gln Gly Asn Val Phe Ser Cys Ser Val Met His Glu Ala
                245                 250                 255

Leu His Asn His Tyr Thr Gln Lys Ser Leu Ser Leu Ser Pro Gly Lys
                260                 265                 270
```

TARGETING CONSTRUCTS

CROSS-REFERENCE TO RELATED APPLICATIONS

This application is a continuation of U.S. patent application Ser. No. 13/814,329, filed Feb. 5, 2013, which is the national stage application of corresponding international application number PCT/EP2011/063720, filed Aug. 9, 2011, which claims priority to and the benefit of European application no. 10172318.7, filed Aug. 9, 2010, all of which are hereby incorporated by reference in their entirety.

TECHNICAL FIELD

The invention relates in general terms to targeted gas-filled microvesicles and to aqueous suspensions containing said microvesicles, for use in particular in diagnostic methods.

BACKGROUND OF THE INVENTION

Rapid development of contrast agents in the recent years has generated a number of different formulations, which are useful in contrast-enhanced imaging of organs and tissue of human or animal body.

More recently, attention has been given to so-called "molecular imaging", where suitable target specific components are used in the formulation of the contrast agents, for allowing selective contrast-enhanced imaging of organs or tissues. In addition, therapeutic use of contrast agent formulations, optionally in combination with molecular imaging, has also been described.

A class of contrast agents, particularly useful for ultrasound contrast imaging, includes suspensions of gas bubbles of nano- and/or micro-metric size dispersed in an aqueous medium. Of particular interest are those formulations where the gas bubbles are stabilized, for example by using emulsifiers, oils, thickeners or sugars, or by entrapping or encapsulating the gas or a precursor thereof in a variety of systems. These stabilized gas bubbles are generally referred to in the art with various terminologies, depending typically from the stabilizing material employed for their preparation; these terms include, for instance, "microspheres", "microbubbles", "microcapsules" or "microballoons". The term "gas-filled microvesicles", or shortly "microvesicles", as used herein includes any of the above terminology.

The formulations of gas-filled microvesicles can be suitably modified, either for improving the diagnostic effect (e.g. through molecular imaging) and/or for therapeutic purposes, such as drug delivery and/or thrombolysis. For instance, microvesicles can be associated (e.g. by inclusion in their boundary envelope) with therapeutic agents and/or with specific components which are capable to link to a determined target within a patient's body (known as "targeting ligands"). Examples of targeting ligands include, for instance, peptides, proteins, antibodies, aptamers or carbohydrates capable of binding to specific receptors expressed by organs or tissues during pathogenic processes such as, for instance, angiogenesis, inflammation or thrombus formation.

Selectins (in particular P-, L- and E-selectin) are cell adhesion molecules expressed, among others, by vascular endothelium during inflammation processes. Selectin ligands and, in particular, P-selectin glycoprotein ligand-1 (PSGL-1: GenBank Acc. N° Q14242.1), is expressed constitutively on all leukocytes (neutrophiles, monocytes and most lymphocytes) and myeloid cells. As such, it plays a critical role in the tethering of these cells to activated platelets or endothelia expressing P-selectin and, even though with a lower affinity, to E and L-selectin. Examples of P-Selectin ligands are disclosed for instance in U.S. Pat. No. 5,840,679

International Patent Application Publ. No. WO 2008/131217 discloses microbubble compositions comprising targeting ligands directed to P-selectin. In particular, the targeting ligand is a fusion protein comprising a P-selectin ligand and a dimerization domain. In practical embodiments, the Application discloses the use of recombinant P-selectin ligand composed of the amino terminal region of PSGL-1 in a selectin-binding glycoform fused to the Fc portion of human IgG$_1$ (rPSGL-Ig), to be conjugated via biotin-streptavidin binding to biotin containing microbubbles. While said Application does not disclose any exact sequence of the P-Selecting ligand, it refers to examples of P-selectin ligands and fragments thereof disclosed by US Patent Application Publ. No. 2003/0166521.

US 2003/0166521 discloses a PSGL-1 fusion protein (dimPSGL-1), also referred to as recombinant PSGL-Ig (or rPSGL-Ig), produced by truncating the N-term 47 amino acids of mature PSGL-1 and linking said N-term 47 amino acids of PSGL-1 to a Fc portion of human immunoglobulin G-1 (IgG$_1$).

The Applicant has now observed that microvesicles bearing only a fragment of said rPSGL-1 protein may have some advantages when compared with microvesicles bearing the complete protein, for instance in terms of binding efficacy and/or in terms of stability of an aqueous suspension containing the microvesicles.

SUMMARY OF THE INVENTION

An aspect of the invention relates to an aqueous suspension of gas-filled microvesicles associated with a polypeptide consisting of a sequence of at most 200 amino acid residues and comprising at least amino acids 5-16 as set forth in SEQ ID NO:1.

Preferably said polypeptide is associated with a component of the microvesicle, more preferably through a covalent bond.

Preferably, said polypeptide comprises at least amino acid 1-19 as set forth in SEQ ID NO: 1, more preferably at least amino acid 5-41 as set forth in SEQ ID NO: 1, and even more preferably at least amino acid 1-47 as set forth in SEQ ID NO: 1.

According to a preferred embodiment, said polypeptide comprises at most 100 amino acid residues, more preferably at most 75 amino acid residues.

According to a preferred embodiment, said polypeptide consists of the amino acid sequence of formula (I):

$$(X^A)_n—Y—(X^B)_m \qquad (I)$$

wherein:
$(X^A)_n$ represents a sequence of n amino acids $X^A$, comprising at least amino acids 5-16 as set forth in SEQ ID NO:1, where:
  n is an integer of from 12 to 199; and
  $X^A$ represents any amino acid with the exception of lysine;
$(X^B)_m$ represents a sequence of m amino acids $X^B$, where;
  m is an integer of from 0 to 10, with the proviso that the sum m+n is at most 199; and
  $X^B$ represents any amino acid with the exception of lysine and cysteine; and
Y represents an amino acid comprising a reactive moiety for associating the polypeptide with a component of the microvesicle.

Preferably the reactive moiety of the Y residue is —NH$_2$ or —SH; more preferably Y is lysine or cysteine, even more preferably lysine.

According to a further preferred embodiment, said polypeptide is represented by a sequence of formula (II):

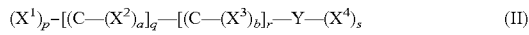
$$(X^1)_p-[(C-(X^2)_a]_q-[(C-(X^3)_b]_r-Y-(X^4)_s \qquad (II)$$

wherein
C represents Cysteine;
Y represents Lysine or Cysteine, preferably Lysine;
$(X^1)_p$ represents a sequence of p amino acids $X^1$ comprising at least amino acids 5-16 as set forth in SEQ ID NO:1, $(X^2)_a$ represents a sequence of a amino acids $X^2$, $(X^3)_b$ represents a sequence of b amino acids $X^3$, $(X^4)_s$ represents a sequence of s amino acids $X^2$, where:
$X^1$, $X^2$, $X^3$, $X^4$ independently represent any amino acid with the exception of lysine and cysteine;
p is an integer of from 12 to 199, preferably from 12 to 99, more preferably 12 to 74;
a and b are independently an integer of from 0 to 50, preferably 0 to 20 and more preferably from 0 to 10;
q and r are independently 0 or 1, at least one being 1; and
s is an integer of from 0 to 10;
with the proviso that the sum p+(a·q)+(b·r)+s is at most 199, preferably at most 99 and even more preferably 74, The above illustrated polypeptides preferably comprise at least one O-glycan moiety and/or at least one sulfate residue bound to an amino acid of the sequence.

According to a preferred embodiment of the invention, the above illustrated polypeptide is in dimeric form, preferably in homodimeric form.

According to a particularly preferred embodiment, said polypeptide consists of a sequence as set forth in SEQ ID NO:3. Preferably, the two cysteine residues of the sequence may bind to respective cysteine residues of a corresponding sequence, to provide the polypeptide in dimeric form.

The invention further relates to precursors of said gas-filled microvesicles, in the form of a dry powder or lyophilized residue. Said precursor is in particular reconstitutable in the presence of a gas by contacting it with a physiologically acceptable aqueous carrier, to form an aqueous suspension of said gas-filled microvesicles upon agitation of the mixture.

A further aspect of the invention relates to a pharmaceutical kit comprising a precursor of said gas-filled microvesicles and a physiologically acceptable aqueous carrier.

DETAILED DESCRIPTION OF THE INVENTION

The term "gas-filled microvesicles" includes any structure comprising bubbles of gas of micrometric or nanometric size surrounded by an envelope or layer (including film-forming layers) of a stabilizing material. The term includes what is known in the art as gas-filled liposomes, microbubbles, microspheres, microballoons or microcapsules. The microvesicles are typically suspended in an aqueous carrier, in particular a physiologically acceptable aqueous carrier. The stabilizing material can be any material typically known in the art including, for instance, surfactants, lipids, sphingolipids, oligolipids, phospholipids, proteins, polypeptides, carbohydrates, and synthetic or natural polymeric materials.

The term "microbubbles" includes bubbles of gas suspended in an aqueous carrier, which are bound at the gas/liquid interface by a very thin envelope (film) involving a stabilizing amphiphilic material disposed at the gas to liquid interface (sometimes referred to in the art as an "evanescent" envelope). Microbubble suspensions can be prepared by contacting a suitable precursor thereof, such as powdered amphiphilic materials (e.g. freeze-dried preformed liposomes or freeze-dried or spray-dried phospholipid dispersions or solutions) with air or other gas and then with an aqueous carrier, while agitating to generate a microbubble suspension which can then be administered, preferably shortly after its preparation. Examples of aqueous suspensions of gas microbubbles, of precursors and of the preparation thereof are disclosed, for instance, in U.S. Pat. Nos. 5,271,928, 5,445,813, 5,413,774, 5,556,610, 5,597,549, 5,827,504 and WO 04/069284, which are here incorporated by reference in their entirety.

The terms "microballoons" or "microcapsules" include suspensions in which the bubbles of gas are surrounded by a solid material envelope of a lipid or of natural or synthetic polymers. Examples of microballoons and of the preparation thereof are disclosed, for instance, in U.S. Pat. Nos. 5,711,933 and 6,333,021.

The term polypeptide as used herein includes sequences of amino acids, which can be either synthetic or preferably natural amino acids.

The term "targeting ligand" includes any compound, moiety or residue having, or being capable of promoting a targeting activity towards tissues and/or receptors in vivo. Targets with which a targeting ligand may be associated include tissues such as, for instance, myocardial tissue (including myocardial cells and cardiomyocytes), membranous tissues (including endothelium and epithelium), laminae, connective tissue (including interstitial tissue) or tumors; blood clots; and receptors such as, for instance, cell-surface receptors for peptide hormones, neurotransmitters, antigens, complement fragments and immunoglobulins. The term includes in particular polypeptides comprising amino acid sequences which exhibit binding affinity ("active sequences") for selectins, particularly for P-selectin; said active sequences include for instance amino acids 5-16, 1-19, 5-41 and 1-47 as set forth in SEQ ID NO: 1.

The term "targeted gas-filled microvesicle" includes any gas-filled microvesicle comprising at least one targeting ligand in its formulation.

The phrase "intermediate of a targeted gas-filled microvesicle" includes any gas-filled microvesicle which can be converted into a targeted gas-filled microvesicle. Such intermediate may include, for instance, gas-filled microvesicles (or precursors thereof) including a suitable reactive moiety (e.g. maleimide), which can be reacted with a corresponding complementary reactive (e.g. thiol) linked to a targeting ligand.

The expression "Fc region" indicates the crystallizable fragment of an immunoglobulin (Ig) composed of the carboxy-terminal halves of both heavy chains linked to each other by disulfide bonds. Fc fragments are different for each immunoglobulin class (i.e. IgG, IgM, IgA, etc.) and type (IgG$_1$, IgG$_2$ etc.).

The term "full length Fc domain" indicates a domain composed of two heavy chains that comprise two or three constant domains depending on the class of the antibody. By binding to specific proteins the Fc domain ensures that each antibody generates an appropriate immune response for a given antigen. This Fc domain also binds to various cell receptors, such as Fc receptors, and other immune molecules, such as complement proteins. By doing this, it mediates different physiological effects including opsonization, cell lysis, and degranulation of mast cells, basophils and eosinophils. Full length Fc domain sequences comprise either unmodified (original) amino acid sequences or corresponding amino acid sequences where one or more non essential amino acids have been mutated. For instance, amino acid sequence 49 to 272 of SEQ ID NO:4 corresponds to the full length Fc domain of IgG$_1$ immunoglobulin, with the two exceptions of amino acids 59 and 62 (where Leu and Gly residues of the original Fc sequence have both been replaced by Ala residues).

The term "therapeutic agent" includes within its meaning any compound, moiety or residue which can be used in any therapeutic application, such as in methods for the treatment of a disease in a patient, as well as any substance which is capable of exerting or responsible to exert a biological effect in vitro and/or in vivo. Therapeutic agents thus include any compound or material capable of being used in the treatment (including prevention, alleviation, pain relief or cure) of any pathological status in a patient (including malady, affliction, disease, lesion or injury). Examples of therapeutic agents are drugs, pharmaceuticals, bioactive agents, cytotoxic agents, chemotherapy agents, radiotherapeutic agents, proteins, natural or synthetic peptides, including oligopeptides and polypeptides, vitamins, steroids and genetic material, including nucleosides, nucleotides, oligonucleotides, polynucleotides and plasmids.

The expression "physiologically acceptable aqueous carrier" includes liquid carriers which are generally employed for injections, such as, for instance, water, typically sterile, pyrogen free water (to prevent as much as possible contamination in the intermediate lyophilized product), aqueous solutions such as saline (which may advantageously be balanced so that the final product for injection is not hypotonic), or aqueous solutions of one or more tonicity adjusting substances such as salts or sugars, sugar alcohols, glycols or other non-ionic polyol materials (eg. glucose, sucrose, sorbitol, mannitol, glycerol, polyethylene glycols, propylene glycols and the like).

Gas-Filled Microvesicles

According to an embodiment of the present invention, the gas-filled microvesicles associated with a targeting ligand as above defined are microbubbles.

Components suitable for forming a stabilizing envelope of microbubbles comprise, for instance, phospholipids; lysophospholipids; fatty acids, such as palmitic acid, stearic acid, arachidonic acid or oleic acid; lipids bearing polymers, such as chitin, hyaluronic acid, polyvinylpyrrolidone or polyethylene glycol (PEG), also referred as "pegylated lipids"; lipids bearing sulfonated mono- di-, oligo- or polysaccharides; cholesterol, cholesterol sulfate or cholesterol hemisuccinate; tocopherol hemisuccinate; lipids with ether or ester-linked fatty acids; polymerized lipids; diacetyl phosphate; dicetyl phosphate; ceramides; polyoxyethylene fatty acid esters (such as polyoxyethylene fatty acid stearates), polyoxyethylene fatty alcohols, polyoxyethylene fatty alcohol ethers, polyoxyethylated sorbitan fatty acid esters, glycerol polyethylene glycol ricinoleate, ethoxylated soybean sterols, ethoxylated castor oil or ethylene oxide (EO) and propylene oxide (PO) block copolymers; sterol aliphatic acid esters including, cholesterol butyrate, cholesterol iso-butyrate, cholesterol palmitate, cholesterol stearate, lanosterol acetate, ergosterol palmitate, or phytosterol n-butyrate; sterol esters of sugar acids including cholesterol glucuronides, lanosterol glucoronides, 7-dehydrocholesterol glucoronide, ergosterol glucoronide, cholesterol gluconate, lanosterol gluconate, or ergosterol gluconate; esters of sugar acids and alcohols including lauryl glucoronide, stearoyl glucoronide, myristoyl glucoronide, lauryl gluconate, myristoyl gluconate, or stearoyl gluconate; esters of sugars with aliphatic acids including sucrose laurate, fructose laurate, sucrose palmitate, sucrose stearate, glucuronic acid, gluconic acid or polyuronic acid; saponins including sarsasapogenin, smilagenin, hederagenin, oleanolic acid, or digitoxigenin; glycerol or glycerol esters including glycerol tripalmitate, glycerol distearate, glycerol tristearate, glycerol dimyristate, glycerol trimyristate, glycerol dilaurate, glycerol trilaurate, glycerol dipalmitate; long chain alcohols including n-decyl alcohol, lauryl alcohol, myristyl alcohol, cetyl alcohol, or n-octadecyl alcohol; 6-(5-cholesten-3β-yloxy)-1-thio-β-D-galactopyranoside; digalactosyldiglyceride; 6-(5-cholesten-3β-yloxy)hexyl-6-amino-6-deoxy-1-thio-β-D-galactopyranoside; 6-(5-cholesten-3β-yloxy)hexyl-6-amino-6-deoxyl-1-thio-β-D-mannopyranoside; 12-(((7'-diethylaminocoumarin-3-yl)carbonyl)methylamino)octadecanoic acid; N-[12-(((7'-diethylaminocoumarin-3-yl)carbonyl)methylamino) octadecanoyl]-2-aminopalmitic acid; N-succinyldioleylphosphatidylethanolamine; 1,2-dioleyl-sn-glycerol; 1,2-dipalmitoyl-sn-3-succinylglycerol; 1,3-dipalmitoyl-2-succinylglycerol; 1-hexadecyl-2-palmitoylglycerophosphoethanolamine or palmitoylhomocysteine; alkylamines or alkylammonium salts, comprising at least one ($C_{10}$-$C_{20}$), preferably ($C_{14}$-$C_{18}$), alkyl chain, such as, for instance, N-stearylamine, N,N'-distearylamine, N-hexadecylamine, N,N'-dihexadecylamine, N-stearylammonium chloride, N,N'-distearylammonium chloride, N-hexadecylammonium chloride, N,N'-dihexadecylammonium chloride, dimethyldioctadecylammonium bromide (DDAB), hexadecyltrimethylammonium bromide (CTAB); tertiary or quaternary ammonium salts comprising one or preferably two ($C_{10}$-$C_{20}$), preferably ($C_{14}$-$C_{18}$), acyl chain linked to the N-atom through a ($C_3$-$C_6$) alkylene bridge, such as, for instance, 1,2-distearoyl-3-trimethylammonium-propane (DPTAP), 1,2-dipalmitoyl-3-trimethylammonium-propane (DPTAP), 1,2-oleoyl-3-trimethylammonium-propane (DOTAP), 1,2-distearoyl-3-dimethylammonium-propane (DSDAP); and mixtures or combinations thereof.

Depending on the combination of components and on the manufacturing process of the microbubbles, the above listed exemplary compounds may be employed as the main compound for forming the microbubble's envelope or as simple additives, thus being present only in minor amounts.

According to a preferred embodiment, at least one of the compounds forming the microbubbles' envelope is an amphiphilic compound (i.e. an organic molecule comprising both a hydrophilic and lipophilic moiety), preferably a phospholipid, optionally in admixture with any of the other above-cited materials. According to the present description, the term phospholipid is intended to encompass any amphiphilic phospholipid compound, the molecules of which are capable of forming a stabilizing film of material (typically in the form of a mono-molecular layer) at the gas-water boundary interface in the final microbubbles suspension. Accordingly, these materials are also referred to in the art as "film-forming phospholipids".

Amphiphilic phospholipid compounds typically contain at least one phosphate group and at least one, preferably two, lipophilic long-chain hydrocarbon groups.

Examples of suitable phospholipids include esters of glycerol with one or preferably two (equal or different) residues of fatty acids and with phosphoric acid, wherein the phosphoric acid residue is in turn bound to a hydrophilic group, such as, for instance, choline (phosphatidylcholines—PC), serine (phosphatidylserines—PS), glycerol (phosphatidylglycerols—PG), ethanolamine (phosphatidylethanolamines—PE), inositol (phosphatidylinositol—PI). Esters of phospholipids with only one residue of fatty acid are generally referred to in the art as the "lyso" forms of the phospholipid or "lysophospholipids". Fatty acids residues present in the phospholipids are in general long chain aliphatic acids, typically containing from 12 to 24 carbon atoms, preferably from 14 to 22; the aliphatic chain may contain one or more unsaturations or is preferably completely saturated. Examples of suitable fatty acids included in the phospholipids are, for instance, lauric acid, myristic acid, palmitic acid, stearic acid, arachidic acid, behenic acid, oleic acid, linoleic acid, and linolenic acid. Preferably, saturated fatty acids such as myristic acid, palmitic acid, stearic acid and arachidic acid are employed.

Further examples of phospholipids are phosphatidic acids, i.e. the diesters of glycerol-phosphoric acid with fatty acids; sphingolipids such as sphingomyelins, i.e. those phosphatidylcholine analogs where the residue of glycerol diester with fatty acids is replaced by a ceramide chain; cardiolipins, i.e. the esters of 1,3-diphosphatidylglycerol with a fatty acid; glycolipids such as gangliosides GM1 (or GM2) or cerebrosides; glucolipids; sulfatides and glycosphingolipids.

As used herein, the term phospholipids include either naturally occurring, semisynthetic or synthetically prepared products that can be employed either singularly or as mixtures.

Examples of naturally occurring phospholipids are natural lecithins (phosphatidylcholine (PC) derivatives) such as, typically, soya bean or egg yolk lecithins.

Examples of semisynthetic phospholipids are the partially or fully hydrogenated derivatives of the naturally occurring lecithins. Preferred phospholipids are fatty acid di-esters of phosphatidylcholine, ethylphosphatidylcholine, phosphatidylglycerol, phosphatidic acid, phosphatidylethanolamine, phosphatidylserine, phosphatidylinositol or of sphingomyelin.

Examples of preferred phospholipids are, for instance, dilauroyl-phosphatidylcholine (DLPC), dimyristoyl-phosphatidylcholine (DMPC), dipalmitoyl-phosphatidylcholine (DPPC), diarachidoyl-phosphatidylcholine (DAPC), distearoyl-phosphatidylcholine (DSPC), dioleoyl-phosphatidylcholine (DOPC), 1,2 Distearoyl-sn-glycero-3-Ethylphosphocholine (Ethyl-DSPC), dipentadecanoyl-phosphatidylcholine (DPDPC), 1-myristoyl-2-palmitoyl-phosphatidylcholine (MPPC), 1-palmitoyl-2-myristoyl-phosphatidylcholine (PMPC), 1-palmitoyl-2-stearoyl-phosphatidylcholine (PSPC), 1-stearoyl-2-palmitoyl-phosphatidylcholine (SPPC), 1-palmitoyl-2-oleylphosphatidylcholine (POPC), 1-oleyl-2-palmitoyl-phosphatidylcholine (OPPC), dilauroyl-phosphatidylglycerol (DLPG) and its alkali metal salts, diarachidoylphosphatidyl-glycerol (DAPG) and its alkali metal salts, dimyristoylphosphatidylglycerol (DMPG) and its alkali metal salts, dipalmitoylphosphatidylglycerol (DPPG) and its alkali metal salts, distearoylphosphatidylglycerol (DSPG) and its alkali metal salts, dioleoyl-phosphatidylglycerol (DOPG) and its alkali metal salts, dimyristoyl phosphatidic acid (DMPA) and its alkali metal salts, dipalmitoyl phosphatidic acid (DPPA) and its alkali metal salts, distearoyl phosphatidic acid (DSPA), diarachidoylphosphatidic acid (DAPA) and its alkali metal salts, dimyristoyl-phosphatidylethanolamine (DMPE), dipalmitoylphosphatidylethanolamine (DPPE), distearoyl phosphatidyl-ethanolamine (DSPE), dioleylphosphatidyl-ethanolamine (DOPE), diarachidoylphosphatidyl-ethanolamine (DAPE), dilinoleylphosphatidylethanolamine (DLPE), dimyristoyl phosphatidylserine (DMPS), diarachidoyl phosphatidylserine (DAPS), dipalmitoyl phosphatidylserine (DPPS), distearoylphosphatidylserine (DSPS), dioleoylphosphatidylserine (DOPS), dipalmitoyl sphingomyelin (DPSP), and distearoylsphingomyelin (DSSP), dilauroyl-phosphatidylinositol (DLPI), diarachidoylphosphatidylinositol (DAPI), dimyristoylphosphatidylinositol (DMPI), dipalmitoylphosphatidylinositol (DPPI), distearoylphosphatidylinositol (DSPI), dioleoyl-phosphatidylinositol (DOPI).

Suitable phospholipids further include phospholipids modified by linking a hydrophilic polymer, such as polyethyleneglycol (PEG) or polypropyleneglycol (PPG), thereto. Preferred polymer-modified phospholipids include "pegylated phospholipids", i.e. phospholipids bound to a PEG polymer. Examples of pegylated phospholipids are pegylated phosphatidylethanolamines ("PE-PEGs" in brief) i.e. phosphatidylethanolamines where the hydrophilic ethanolamine moiety is linked to a PEG molecule of variable molecular weight (e.g. from 300 to 20000 daltons, preferably from 500 to 5000 daltons), such as DPPE-PEG (or DSPE-PEG, DMPE-PEG, DAPE-PEG or DOPE-PEG). For example, DPPE-PEG2000 refers to DPPE having attached thereto a PEG polymer having a mean average molecular weight of about 2000.

Particularly preferred phospholipids are DAPC, DSPC, DSPG, DPPA, DSPA, DMPS, DPPS, DSPS and Ethyl-DSPC. Most preferred are DSPG or DSPC.

Mixtures of phospholipids can also be used, such as, for instance, mixtures of DSPE, DPPE, DPPC, DSPC and/or DAPC with DSPS, DPPS, DSPA, DPPA, DSPG, DPPG, Ethyl-DSPC and/or Ethyl-DPPC.

In preferred embodiments, the phospholipid is the main component of the stabilizing envelope of microbubbles, amounting to at least 50% (w/w) of the total amount of components forming the envelope of the gas-filled microbubbles. In some of the preferred embodiments, substantially the totality of the envelope (i.e. at least 80% and up to 100% by weight) can be formed of phospholipids.

The phospholipids can conveniently be used in admixture with any of the above listed compounds. Thus, for instance, substances such as cholesterol, ergosterol, phytosterol, sitosterol, lanosterol, tocopherol, propyl gallate or ascorbyl palmitate, fatty acids such as myristic acid, palmitic acid, stearic acid, arachidic acid and derivatives thereof or butylated hydroxytoluene and/or other non-phospholipid compounds can optionally be added to one or more of the foregoing phospholipids in proportions ranging from zero to 50% by weight, preferably up to 25%. Particularly preferred are amphiphilic compounds, such as $C_{10}$-$C_{20}$ carboxylic acids, preferably palmitic acid.

According to a preferred embodiment, the envelope of microbubbles according to the invention includes a compound bearing an overall (positive or negative) net charge. Said compound can be a charged amphiphilic material, preferably a lipid or a phospholipid.

Examples of phospholipids bearing an overall negative charge are derivatives, in particular fatty acid di-ester derivatives, of phosphatidylserine, such as DMPS, DPPS, DSPS; of phosphatidic acid, such as DMPA, DPPA, DSPA; of phosphatidylglycerol such as DMPG, DPPG and DSPG or of phosphatidylinositol, such as DMPI, DPPI or DPPI. Also modified phospholipids, in particular PEG-modified phosphatidylethanolamines, such as DPPE-PEG or DSPE-PEG, can be used as negatively charged molecules. Also the lyso-form of the above cited phospholipids, such as lysophosphatidylserine derivatives (e.g. lyso-DMPS, -DPPS -DSPS), lysophosphatidic acid derivatives (e.g. lyso-DMPA, -DPPA or -DSPA) and lysophosphatidylglycerol derivatives (e.g. lyso-DMPG, -DPPG or -DSPG), can advantageously be used as negatively charged compounds. Other examples of negatively charged compounds are bile acid salts such as cholic acid salts, deoxycholic acid salts or glycocholic acid salts; and ($C_{12}$-$C_{24}$), preferably ($C_{14}$-$C_{22}$) fatty acid salts such as, for instance, palmitic acid salts, stearic acid salts, 1,2-dipalmitoyl-sn-3-succinylglycerol salts or 1,3-dipalmitoyl-2-succinylglycerol salts.

Preferably, the negatively charged compound is selected among DPPA, DPPS, DSPG, DPPG, DSPE-PEG2000, DSPE-PEG5000 or mixtures thereof.

The negatively charged component is typically associated with a corresponding positive counter-ion, which can be mono- (e.g. an alkali metal or ammonium), di- (e.g. an alkaline earth metal) or tri-valent (e.g. aluminium). Preferably the counter-ion is selected among alkali metal cations, such as $Na^+$ or $K^+$, more preferably $Na^+$.

Examples of phospholipids bearing an overall positive charge are derivatives of ethylphosphatidylcholine, in particular di-esters of ethylphosphatidylcholine with fatty acids, such as 1,2-distearoyl-sn-glycero-3-ethylphosphocholine (Ethyl-DSPC or DSEPC), 1,2-dipalmitoyl-sn-glycero-3-ethylphosphocholine (Ethyl-DPPC or DPEPC). The negative counterion is preferably a halide ion, in particular chloride or bromide ion. Examples of positively charged compounds that can be incorporated into the envelope of microbubbles are mono-, di- tri-, or tetra-alkylammonium salts with a halide counter ion (e.g. chloride or bromide) comprising at least one ($C_{10}$-$C_{20}$), preferably ($C_{14}$-$C_{18}$), alkyl chain, such as, for instance mono- or di-stearylammonium chloride, mono or di-hexadecylammonium chloride, dimethyldioctadecylammonium bromide (DDAB) or hexadecyltrimethylammonium bromide (CTAB). Further examples of positively charged compounds that can be incorporated into the envelope of microbubbles are tertiary or quaternary ammonium salts with a halide counter ion (e.g. chloride or bromide) comprising one or preferably two ($C_{10}$-$C_{20}$), preferably ($C_{14}$-$C_{18}$), acyl chains linked to the N-atom through a ($C_3$-$C_6$) alkylene bridge, such as, for instance, 1,2-distearoyl-3-trimethylammonium-propane (DSTAP), 1,2-dipalmitoyl-3-trimethylammonium-propane (DPTAP), 1,2-oleoyl-3-trimethylammonium-propane (DOTAP) or 1,2-distearoyl-3-dimethylammonium-propane (DSDAP).

DSEPC, DPEPC and/or DSTAP are preferably employed as positively charged compounds in the microbubble envelope.

The positively charged component is typically associated with a corresponding negative counter-ion, which can be mono- (e.g. halide), di- (e.g. sulphate) or tri-valent (e.g. phosphate). Preferably the counter-ion is selected from among the halide ions, such as $F^-$ (fluorine), $Cl^-$ (chlorine) or $Br^-$ (bromine).

Mixtures of neutral and charged compounds, in particular of phospholipids and/or lipids, can be satisfactorily employed to form the microbubble envelope. The amount of charged lipid or phospholipid may vary from about 95 mol % to about 0.1 mol %, with respect to the total amount of lipid and phospholipid, preferably from 80 mol % to 0.5 mol %.

Preferred mixtures of neutral phospholipids and charged lipids or phospholipids are, for instance, DPPG/DSPC, DSTAP/DAPC, DPPS/DSPC, DPPS/DAPC, DPPE/DPPG, DSPA/DAPC, DSPA/DSPC and DSPG/DSPC.

Any of the above illustrated components useful for forming the stabilizing envelope of the gas-filled microvesicle, in particular phospholipids, preferably pegylated phospholipids, can be modified by inserting a suitable reactive moiety therein, in order to allow binding suitable compounds, such as a targeting ligand comprising the sequence of amino acids set forth as SEQ ID NO:1. For instance, a pegylated phospholipid (e.g. DSPE-PEG2000) may comprise a terminal reactive moiety (e.g. maleimide, in brief "mal", thus forming a DSPE-PEG-mal component) capable of (covalently) reacting with a corresponding reactive moiety on a compound comprising the above sequence. Examples of additional suitable reactive moieties are illustrated in the following of this specification.

According to an alternative embodiment, the targeting ligand component can be associated with gas-filled microcapsules. Preferred examples of microcapsules are those having a stabilizing envelope comprising a polymer, preferably a biodegradable polymer, or a biodegradable water-insoluble lipid (such as tripalmitine) optionally in admixture with a biodegradable polymer. Examples of suitable microcapsules and of the preparation thereof are disclosed, for instance in U.S. Pat. Nos. 5,711,933 and 6,333,021, herein incorporated by reference in their entirety. Microcapsules having a proteinaceous envelope, i.e. made of natural proteins (albumin, haemoglobin) such as those described in U.S. Pat. No. 4,276,885 or EP-A-0 324 938 (here incorporated by reference), can also be employed. The targeting ligand can be incorporated into the microcapsules e.g. by binding it to an envelope-forming component of the microcapsules, according to the preparation methods illustrated above, or by admixing to the components forming the microcapsules envelope an amphiphilic component, as those previously illustrated, covalently bound to targeting ligand.

Other excipients or additives may be present either in the dry formulation of the microvesicles or may be added together with the aqueous carrier used for the reconstitution thereof, without necessarily being involved (or only partially involved) in the formation of the stabilizing envelope of the microvesicles. These include pH regulators (such as histidine), osmolality adjusters, viscosity enhancers, emulsifiers, bulking agents, etc. and may be used in conventional amounts. For instance compounds like polyoxypropylene glycol and polyoxyethylene glycol as well as copolymers thereof can be used. Examples of viscosity enhancers or stabilizers are compounds selected from linear and cross-linked poly- and oligo-saccharides, sugars and hydrophilic polymers such as polyethylene glycol.

As the preparation of gas-filled microvesicles may involve a freeze drying or spray drying step, it may be advantageous to include in the formulation a lyophilization additive, such as an agent with cryoprotective and/or lyoprotective effect and/or a bulking agent, for example an amino-acid such as glycine; a carbohydrate, e.g. a sugar such as sucrose, mannitol, maltose, trehalose, glucose, lactose or a cyclodextrin, or a polysaccharide such as dextran; or a polyoxyalkyleneglycol such as polyethylene glycol. Typically, the amount of the lyophilization additive may range from about 10 to about 1000 times (w/w) the amount of the microvesicle-forming components.

Any biocompatible gas, gas precursor or mixture thereof may be employed to fill the above microvesicles (hereinafter also identified as "microvesicle-forming gas").

The gas may comprise, for example, air; nitrogen; oxygen; carbon dioxide; hydrogen; nitrous oxide; a noble or inert gas such as helium, argon, xenon or krypton; a radioactive gas such as $Xe^{133}$ or $Kr^{81}$; a hyperpolarized noble gas such as hyperpolarized helium, hyperpolarized xenon or hyperpolarized neon; a low molecular weight hydrocarbon (e.g. containing up to 7 carbon atoms), for example an alkane such as methane, ethane, propane, butane, isobutane, pentane or isopentane, a cycloalkane such as cyclobutane or cyclopentane, an alkene such as propene, butene or isobutene, or an alkyne such as acetylene; an ether; a ketone; an ester; halogenated gases, preferably fluorinated gases, such as or halogenated, fluorinated or perfluorinated low molecular weight hydrocarbons (e.g. containing up to 7 carbon atoms); or a mixture of any of the foregoing. Where a halogenated hydrocarbon is used, preferably at least some, more preferably all, of the halogen atoms in said compound are fluorine atoms.

Fluorinated gases are preferred, in particular perfluorinated gases, especially in the field of ultrasound imaging. Fluorinated gases include materials which contain at least one fluorine atom such as, for instance fluorinated hydrocarbons (organic compounds containing one or more carbon atoms and fluorine); sulfur hexafluoride; fluorinated, preferably perfluorinated, ketones such as perfluoroacetone; and fluorinated, preferably perfluorinated, ethers such as perfluorodiethyl ether. Preferred compounds are perfluorinated gases, such as $SF_6$ or perfluorocarbons (perfluorinated hydrocarbons), i.e. hydrocarbons where all the hydrogen atoms are replaced by fluorine atoms, which are known to form particularly stable microbubble suspensions, as disclosed, for instance, in EP 0554 213, which is herein incorporated by reference.

The term perfluorocarbon includes saturated, unsaturated, and cyclic perfluorocarbons. Examples of biocompatible, physiologically acceptable perfluorocarbons are: perfluoroalkanes, such as perfluoromethane, perfluoroethane, perfluoropropanes, perfluorobutanes (e.g. perfluoro-n-butane, optionally in admixture with other isomers such as perfluoroisobutane), perfluoropentanes, perfluorohexanes or perfluoroheptanes; perfluoroalkenes, such as perfluoropropene, perfluorobutenes (e.g. perfluorobut-2ene) perfluorobutadiene; perfluoroalkynes (e.g. perfluorobut-2-yne); and perfluorocycloalkanes (e.g. perfluorocyclobutane, perfluoromethylcyclobutane, perfluorodimethylcyclobutanes, perfluorotrimethylcyclobutanes, perfluorocyclopentane, perfluoromethylcyclopentane, perfluorodimethylcyclopentanes, perfluorocyclohexane, perfluoromethylcyclohexane and perfluorocycloheptane). Preferred saturated perfluorocarbons include, for example, $CF_4$, $C_2F_6$, $C_3F_8$, $C_4F_8$, $C_4F_{10}$, $C_5F_{12}$ and $C_6F_{12}$.

It may also be advantageous to use a mixture of any of the above gases in any ratio. For instance, the mixture may comprise a conventional gas, such as nitrogen, air or carbon dioxide and a gas forming a stable microbubble suspension, such as sulfur hexafluoride or a perfluorocarbon as indicated above. Examples of suitable gas mixtures can be found, for instance, in WO 94/09829, which is herein incorporated by reference. The following combinations are particularly preferred: a mixture of gases (A) and (B) in which the gas (B) is a fluorinated gas, selected among those previously illustrated, including mixtures thereof, and (A) is selected from air, oxygen, nitrogen, carbon dioxide or mixtures thereof. The amount of gas (B) can represent from about 0.5% to about 95% v/v of the total mixture, preferably from about 5% to 80%.

Particularly preferred gases are $SF_6$, $C_3F_8$, $C_4F_{10}$ or mixtures thereof, optionally in admixture with air, oxygen, nitrogen, carbon dioxide or mixtures thereof.

In certain circumstances it may be desirable to include a precursor to a gaseous substance (i.e. a material that is capable of being converted to a gas in vivo). Preferably the gaseous precursor and the gas derived therefrom are physiologically acceptable. The gaseous precursor may be pH-activated, photo-activated, temperature activated, etc. For example, certain perfluorocarbons may be used as temperature activated gaseous precursors. These perfluorocarbons, such as perfluoropentane or perfluorohexane, have a liquid/gas phase transition temperature above room temperature (or the temperature at which the agents are produced and/or stored) but below body temperature; thus, they undergo a liquid/gas phase transition and are converted to a gas within the human body.

For the use in MRI the microvesicles will preferably contain a hyperpolarized noble gas such as hyperpolarized neon, hyperpolarized helium, hyperpolarized xenon, or mixtures thereof, optionally in admixture with air, carbon dioxide, oxygen, nitrogen, helium, xenon, or any of the halogenated hydrocarbons as defined above.

For use in scintigraphy, the microvesicle will preferably contain radioactive gases such as $Xe^{133}$ or $Kr^{81}$ or mixtures thereof, optionally in admixture with air, carbon dioxide, oxygen, nitrogen, helium, kripton or any of the halogenated hydrocarbons as defined above.

Targeting Ligand

The polypeptide associated with a microvesicle according to the present invention comprises at least a portion of the sequence of amino acids as set forth in SEQ ID NO: 1 which exhibits binding affinity for selectins, particularly for P-selectin. In particular, said polypeptide comprises at least amino acids 5-16 of SEQ ID NO: 1, corresponding to amino acids 46-57 of the "P-selectin glycoprotein ligand-1" (PSGL-1, GenBank Acc. N° Q14242.1). According to a preferred embodiment, the targeting ligand comprises at least amino acids 1-19, more preferably at least amino acids 5-41 and even more preferably at least amino acids 1-47 as set forth in SEQ ID NO: 1 (these latters corresponding to amino acids 42-88 of the "P-selectin glycoprotein ligand -1").

"P-selectin glycoprotein ligand-1" and polypeptides comprising the active sequences illustrated above, including SED ID NO: 1, preferably comprise a glycan residue bound to at least one amino acid of said sequences.

The term "glycan residue" comprises O-linked glycan residues (linked to the oxygen atom of hydroxyl groups of amino acid residues such as serine, threonine, tyrosine, hydroxytyrosine or hydroxyproline) and N-linked glycan residues (linked to the nitrogen atom of tertiary amino groups of amino acids, such as asparagine).

O-linked glycans typically comprise sugar residues such as N-acetylgalactosamine, N-acetylglucosamine (GlcNAc), fucose, glucose, mannose (Man), hexose, xylose, sialic acid or mixtures thereof. O-linked glycans preferably consist of a sialyl Lewis x structure ($sLe^x$, sialic acid-galactopyranosyl-fucose-N-acetylglucosamine).

N-linked glycans typically comprise a pentasaccharidic core (Man3GlcNAc2). Complex type chains may present a mono-, bi-, tri- (2,4 and 2,6 branched), tetra-, and pentaantennary structures. They may further comprise various saccharides such as, galactose, sialic acid, N-acetylglucosamine, mannose, fucose and combinations of thereof.

The polypeptide associated with a microvesicle of the present invention preferably contains one or more of the following glycans (or mixtures thereof) bound to an amino acid of the sequence:

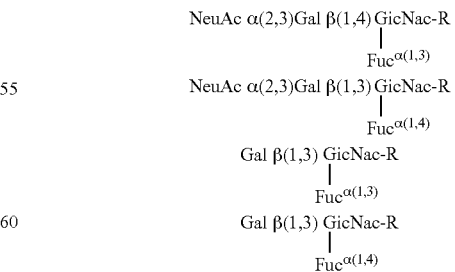

wherein:
R is either a bond or represents any other glycan as above defined; NeuAc is neuraminic acid; Gal is galactose; GlcNAc is N-acetylglucosamine and Fuc is fucose.

Amino acids residues of SEQ ID NO:1 which may optionally bear a glycan residue as above defined comprise: (a) amino acids in position 16, 25, 26, 28, 29, 32, 36, 39, 40 or 41, preferably bearing O-linked glycan residues; and/or (b) amino acid in position 24 preferably bearing N-linked glycan residues.

Advantageously, SEQ ID NO: 1 may comprise a sialyl Lewis-x (sLe$^x$) bound to threonine at the position 16 (see e.g. R. D Cumming, "Structure and function of selectin ligand PSGL-1", Braz. J. Biol. Res., 32(5) 1999, pp. 520-528).

Furthermore, at least one tyrosine residue in position 5, 7 and/or 10 of SEQ ID NO: 1 may optionally be sulfated (TyrSO$_3$). More preferably at least two and even more preferably all of the three tyrosine residues may contain a sulfate group.

The polypeptide is an amino acid sequence of from 12 to 200, more preferably of 12 to 100, amino acid residues in length and it comprises a reactive moiety capable of reacting with a corresponding reactive moiety of a microvesicle's component. Particularly preferred is an amino acid sequence of from 12 to 75 amino acid residues, even more preferably of from 12 to 50 residues.

According to a preferred embodiment the polypeptide comprises an amino acid bearing a reactive moiety. Said amino acid is preferably selected from the group consisting of: Cysteine and/or a basic amino acid, preferably Lysine. Preferably, said reactive moiety is at the C-terminal position of the polypeptide, preferably it being Lysine. In a preferred embodiment, the presence of a single reactive moiety (Lysine in particular) at the C-terminus of the polypeptide sequence allows for a controlled functionalization of said group and for subsequent effective reaction condition with a corresponding reactive group on a component of the microvesicle. On the other side, the presence of a plurality of reactive Lysine groups on a peptidic chain (such as in the case of the Fc portion of SEQ ID NO:4) may render the functionalization of said groups much more random, with the result of having a much lower control on which among the various reactive groups of the peptide will bind to the microvesicles' component.

Preferred polypeptides are those represented by formula (I) and more preferably formula (II), as previously illustrated.

In a preferred embodiment, the polypeptide comprises the amino acids of SEQ ID NO: 1 linked to amino acid sequence SEQ ID NO:2 or to a N-terminal fragment thereof, where said fragment corresponds to amino acids 1-20, 1-15, 1-10, 1-5 or 1-4 of SEQ ID NO:2.

When the N-terminal fragment is a single amino acid residue, said amino acid is preferably a proline (Pro).

A particularly preferred embodiment is represented by the fusion polypeptide having SEQ ID NO:3 and consisting of SEQ ID NO:1 covalently bound to SEQ ID NO:2.

The fusion polypeptide can be obtained by enzymatic proteolysis of rPSGL-Ig, for instance by incubating the protein in the presence of a suitable endoproteinase. In a preferred embodiment an endoprotease cleaving peptidyl bonds on the C-terminal side of Lysine residues (e.g. endoproteinase Lys-C) is used. The incubation of the protein with endoproteinase Lys-C allows in particular the removal of a substantial portion of the Fc domain from the mature protein rPSGL-Ig, providing a dimeric sequence containing a single (C-terminal) Lysine residue (amino acid in position 71 in SEQ ID NO: 3 and SEQ ID NO: 4) for each sequence of the dimer, which can advantageously be employed for the subsequent binding procedure of the polypeptide to a suitable microvesicle's component.

Alternatively, the polypeptide can be obtained by production of recombinant protein from a custom made DNA. Briefly, a plasmid is prepared by inserting the cDNA sequence of the desired polypeptide in a plasmid vector. The plasmid vector is then associated with a suitable expression system for producing the recombinant polypeptide (e.g. as set forth in SEQ ID NO:3). Examples of suitable expression systems include mammalian cells, such as CHO cells (Chinese Hamster Ovary cells), HEK293 cells (Human Embryonic Kidney 293 cells), Sp2/0 cells (mouse myeloma cell line), MEL cells (mouse erythroleukemia cells) or COS cells (kidney cells of the monkey carrying the SV40 genetic material); insect cells, such as Sf9 cell lines; virus containing cells such as BEVS cells (Baculovirus Expression Vector System); or plant-based expression systems, such as tobacco leaves, corn, rice cell or transgenic potatoes. Most preferably, CHO cells stably expressing core-2 β1,6N-acetylglucosaminyl-transferase (C2GlcNAcT-I) and α-1,3-fucosyltransferase-VII (fucT-VII) are transfected with the cDNA encoding for the polypeptide. Cells expressing permanently the recombinant polypeptide are selected. Then, these cells are transferred to a bioreactor to allow large scale production of the polypeptide.

In a preferred embodiment the recombinant polypeptide is obtained in dimeric form, in particular in homodimeric form. In general, peptide dimerization is a natural process occurring in the cells expressing the recombinant polypeptide, typically during Posttranslational modification (PTM) of the polypeptide.

The above recombinant preparation technique can be used for preparing a polypeptide according to the invention, which comprises any active sequence amino acid exhibiting binding affinity for selectins, particularly p-selectin, as set forth before (including the polypeptide as set forth in SEQ ID NO:3), preferably in dimeric form. In a particularly preferred embodiment, the method can be used for preparing a polypeptide containing a single Lysine amino acid (preferably in terminal position, particularly in C-terminal position) and comprising any of the above illustrated active sequences.

To provide the preferred dimeric form to be associated with the microvesicle, the polypeptide preferably comprises in its sequence one or more cysteine residues which are bound to one or more respective cysteine residues on a corresponding polypeptide sequence, so to form at least one (preferably at least two) disulfide bridge between the two sequences.

In an alternative embodiment, the polypeptide associated with the microvesicle can be employed in monomeric form. Said monomeric form can be obtained according to conventional procedures, either by direct preparation of the monomeric form or by reduction of disulfide bonds in dimeric polypeptides. For instance, a suitable monomeric form of targeting ligand can be obtained by reducing the disulfide bonds of cysteine residues of a dimeric form, e.g. the sequence set forth as SEQ ID NO:3. The disulfide bond reduction can be performed according to conventional techniques, e.g. by incubating a suspension of the dimeric form in the presence of suitable reducing agents, such as TCEP. The reduction of the disulfide bond has the further advantage of providing a suitable reactive group (—SH) in the ligand, for the subsequent binding to a corresponding moiety on a component of the microvesicle (e.g. PE-PEG-maleimide), without need of introducing a (thiolated) reactive group in the polypeptide.

In an embodiment of the invention, the polypeptide can be bound to the component of the gas-filled microvesicle through a linker. Suitable linkers are preferably hydrophilic residues, typically containing repeating oxyethylene units in the backbone chain.

According to an embodiment, the linker is a moiety of formula (III):

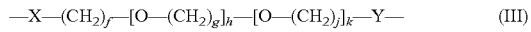

$$-X-(CH_2)_f-[O-(CH_2)_g]_h-[O-(CH_2)_j]_k-Y- \qquad (III)$$

where f, g, h and j independently represent an integer of from 1 to 4, k represents and integer of from 0 to 4, and X and Y respectively represent respective reactive moieties for binding the linker to the polypeptide, at one end, and to the microvesicle's component, at the other end.

The linker comprises suitable reactive moieties at its respective ends, for covalently binding to a corresponding complementary reactive moiety on the microvesicle's component, on one side, and to a corresponding complementary reactive moiety on the polypeptide, for instance on the Y residue of the polypeptide of formula (I), on the other side.

Examples of said reactive moieties include amino groups (—NH$_2$, forming the —NH— binding residue), carboxyl groups (—COOH, forming the —CO— binding residue) or thiol groups (—SH, forming the —S— binding residue). Preferably said binding moiety is an amino or a carboxyl group.

Preferred examples of linkers of formula III are:
—CO—CH$_2$—[O—(CH$_2$)$_2$]$_2$—NH—(Adoa)
—CO—CH$_2$—[O—(CH$_2$)$_2$]$_2$—CO—(Tuda)
—NH—CH$_2$—(CH$_2$—O—CH$_2$)$_3$—CH$_2$—NH—(Ttda)
—CO—CH$_2$—[O—(CH$_2$)$_2$]$_2$—CO—NH—CH$_2$—(CH$_2$—O—CH$_2$)$_3$—CH$_2$—NH—(Ddhh)

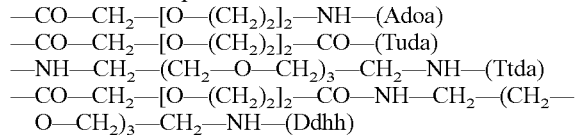

Preferably, said linker is formed by two, equal or different, moieties defined by the above formula.

Examples of combined linkers are:
-Adoa-Adoa- or -Ddhh- (which is comprised of the Ttda- and Tuda-linkers).

Polysaccharides, containing suitable reactive binding moieties, are further examples of suitable linkers.

The sequence comprising SEQ ID NO:1, or active fragments thereof, and the desired linker can be prepared according to conventional peptide synthesis methods.

The polypeptide as above illustrated can be associated with a microvesicle according to any of the procedures known in the art, including for instance, covalent binding, non-covalent interactions of affinity binding pairs (e.g. interaction between avidin or streptavidin on one side and biotin on the other side), electrostatic interactions (e.g. ionic or hydrogen bond) or hydrophobic interactions (e.g. between lipophilic hydrocarbon chains).

Preferably, the polypeptide is covalently bound to a respective component of the gas-filled microvesicle.

For instance, if the polypeptide includes a reactive amino group (e.g. a primary amino group of Lysine), it can be reacted with the microvesicle's component containing a suitable corresponding reactive moiety, such as an isothiocyanate group (to form a thiourea bond), a reactive ester (to form an amide bond), or an aldehyde group (to form an imine bond, which may be reduced to an alkylamine bond).

Alternatively, when the targeting ligand includes a reactive thiol group, suitable complementary reactive moieties on the microvesicle's component may include haloacetyl derivatives, maleimides (to form a thioether bond) or a mixed disulfide comprising a sulphide in the form of a 2-pyridylthio (PDT) group (which, upon reaction with a thiol derived from the targeting ligand, results in the formation of a stable disulfide bond).

Alternatively, according to an embodiment of the invention, a targeting ligand containing an amino reactive moiety (e.g. a secondary amino group, in particular the terminal —NH$_2$ group) can be first reacted with a sulphur-containing compound, to introduce a reactive thiol moiety in the targeting ligand, which is then reacted with a corresponding complementary moiety on the microvesicle's component as above illustrated. Examples of suitable sulphur-containing compounds useful for introducing a reactive thiol moiety in a targeting ligand containing a reactive amino moiety include, for instance: thioimidate (such as Traut's reagent) N-succinimidyl-S-acetylthioacetate (SATA), N-succinimidyl-S-acetylthiopropionate (SATP) or N-succinimidyl 3-(2-pyridyldithio)propionate (SPDP). Detailed description of S-containing agents and respective thiolation reactions can be found, for instance, in the book by Greg T. Hermanson: "Bioconjugate Techniques", Elsevier ed., 2$^{nd}$ ed. (April 2008), chapter 1, section 4-1. For instance, one may prepare a maleimide-derivatized phospholipid (e.g. phosphatidylethanolamine -PE- or pegylated PE) and react it with a targeting ligand (e.g. SEQ ID NO:3) where a secondary amino group (e.g. the —NH$_2$ of terminal Lysine) has been previously reacted with a sulphur-containing compound (such as those previously illustrated), to introduce a reactive thiol moiety; the obtained compound can then be used in the preparation of targeted gas-filled microvesicles.

According to a further alternative, when the targeting ligand includes a reactive carboxylic group, suitable reactive moieties on the microvesicle's component can be amines and hydrazides (to form amide or N-acyl, N'-alkylhydrazide functions).

According to a preferred embodiment, a targeting ligand containing an amino reactive moiety (e.g. on a Lysine residue), can be first reacted with a maleimide-containing compound, to introduce a reactive maleimide moiety in the targeting ligand, which is then reacted with a corresponding complementary moiety on the microvesicle's component. Maleimide-containing agents useful for introducing a reactive maleimide moiety in a targeting ligand containing a reactive amino moiety and respective reaction of addition of maleimide group are well known in the art. Examples of suitable maleimide-containing compounds include, for instance: AMAS (N-(α-maleimidoacetoxy)succinimide ester), BMPS (N-(β-maleimidopropoxyl)succinimide ester), EMCS (N-(ε-maleimidocaproyloxy)succinimide ester), GMBS (N-(γ-maleimidobutyryloxy)succinimide ester), LC-SMCC (succinimidyl-4-(N-maleimidomethyl)-cyclohexane-1-carboxy-(6-amidocaproate)), MBS (m-maleimidobenzoyl-N-hydroxysuccimide ester), SMCC (succinimidyl-4-(N-maleimidomethyl)cyclohexane-1-carboxylate), SMPB (succinimidyl-4-(p-maleimidophenyl)butyrate), SM(PEG)n reagent (succinimidyl-(N-maleimidopropionamido)-ethyleneglycol) ester), SMPH (succinimidyl-6-((β-maleimidopropionamido) hexanoate)), sulfo-EMCS (N-(ε-maleimidocaproyloxy) sulfosuccinimide ester), sulfo-GMBS (N-(γ-maleimidobutyroyloxy)sulfosuccinimide ester), sulfo-KMUS (N-(κ-maleimidoundecanoyloxy)-sulfosuccinimide ester), sulfo-MBS (m-maleimidobenzoyl-N-hydroxysulfosuccinimide ester), sulfo-SMCC (sulfosuccinimidyl 4-(N-maleimidomethyl)-cyclohexane-1-carboxylate), sulfo-SMPB (sulfosuccinimidyl 4-(p-maleimidophenyl(butyrate)). According to a particulalrly preferred embodiment, one may react a thiol-containing phospholipid (e.g. thiolated phosphatidylethanolamine—PE—or pegylated PE) with a targeting ligand (e.g. SEQ ID NO:3) where a secondary amino group (e.g. the NH$_2$of terminal lysine) has been previously reacted with a maleimide-containing compound (such a those previously illustrated), to introduce a reactive maleimide moiety therein; the obtained compound can then be used in the preparation of the microvesicles. The thiol-containing phospholipid can be obtained, for instance, by reacting a 2-pyridyldithio (PDT) group attached to a phospholipid with a reductive agent (such as TCEP (tris(2-carboxyethyl)phosphine hydrochloride) to generate a reactive thiol moiety on the phospholipid. Examples of thiol-containing phospholipids include Sodium 1,2-Dipalmitoyl-sn-Glycero-3-Phosphothioethanol, (from Avanti Polar Lipids, IUPAC: sodium (R)-2,3-bis(palmitoyloxy)propyl(2-mercaptoethyl) phosphonate), or those obtainable by chemical reduction of a respective pyridylthio-precursors, such as: sodium (R)-2,3-bis(palmitoyloxy)propyl (2-(3-mercaptopropanamido)ethyl) phosphate (from sodium 1,2-dipalmitoyl-sn-glycero-3-phosphoethanolamine-N-[3-(2-pyridyldithio)propionate], Avanti Polar Lipids), sodium (R)-2,3-bis(oleoyloxy)propyl (2-(3-mercaptopropanamido)ethyl) phosphate (from sodium 1,2-dioleoyl-sn-glycero-3-phosphoethanolamine-N-[3-(2-pyridyldithio)propionate], Avanti polar Lipids) or ammonium (R)-2,3-bis(stearoyloxy)propyl (2-(((2-(3-mercaptopropanamido) polyethylene glycol 2000)carbonyl)amino)ethyl) phosphate (from 1,2-distearoyl-sn-glycero-3-phosphoethanolamine-N-[PDP(polyethylene glycol)-2000], Avanti Polar Lipids).

In an alternative embodiment, a biotin residue can be introduced on the polypeptide (e.g. by reacting hydrosuccinimidobiotin with the peptide's C-terminal) and the biotinylated peptide is then reacted with a microvesicle comprising a streptavidin-bearing (or avidin-, neutravidin- or extravidibearing) component, such as a pegylated phospholipid containing a streptavidin (or avidin, neutravidin or extravidin) residue.

Targeted Gas-Filled Microvesicles

The targeted microvesicles of a composition according to the invention can be produced according to any known method in the art, as illustrated in the above cited patent documents.

For instance, the manufacturing method of microbubbles may involve the preparation of a dried powdered material comprising an amphiphilic material as indicated above, preferably by lyophilization (freeze drying) of an aqueous and/or organic suspension/emulsion comprising said material. Said dried powdered material, identified in the present specification and claims as "precursor" of the gas-filled microvesicles, is then contacted with a physiologically acceptable solution in the presence of the desired gas, to form the desired suspension of gas-filled microvesicles upon agitation of the mixture.

According to the preparation method described in WO 91/15244, film-forming amphiphilic compounds can be first converted into a lamellar form by any method employed for formation of liposomes. To this end, an aqueous solution comprising the film forming lipids and optionally other additives (e.g. viscosity enhancers, non-film forming surfactants, electrolytes etc.) can be submitted to high-speed mechanical homogenisation or to sonication under acoustic or ultrasonic frequencies, and then freeze dried to form a free flowing powder which is then stored in the presence of a gas. Optional washing steps, as disclosed for instance in U.S. Pat. No. 5,597,549, can be performed before freeze drying.

According to an alternative embodiment (described for instance in U.S. Pat. No. 5,597,549) a film forming compound and a hydrophilic stabiliser (e.g. polyethylene glycol, polyvinyl pyrrolidone, polyvinyl alcohol, glycolic acid, malic acid or maltol) can be dissolved in an organic solvent (e.g. tertiary butanol, 2-methyl-2-butanol or $C_2Cl_4F_2$) and the solution can be freeze-dried to form a dry powder.

Preferably, as disclosed for instance in International patent application WO2004/069284, a phospholipid (selected among those cited above and including at least one of the above-identified charged phospholipids) and a lyoprotecting agent (such as those previously listed, in particular carbohydrates, sugar alcohols, polyglycols, polyoxyalkylene glycols and mixtures thereof) can be dispersed in an emulsion of water with a water immiscible organic solvent (e.g. branched or linear alkanes, alkenes, cyclo-alkanes, aromatic hydrocarbons, alkyl ethers, ketones, halogenated hydrocarbons, perfluorinated hydrocarbons or mixtures thereof) under agitation. The emulsion can be obtained by submitting the aqueous medium and the solvent in the presence of at least one phospholipid to any appropriate emulsion-generating technique known in the art. Preferably, the phospholipid is dispersed in the aqueous medium before this latter is admixed with the organic solvent. Alternatively, the phospholipid can be dispersed in the organic solvent or it may be separately added the aqueous-organic mixture before or during the emulsification step. The so obtained microemulsion, which contains microdroplets of solvent surrounded and stabilized by the phospholipid material (and optionally by other amphiphilic film-forming compounds and/or additives), is then lyophilized according to conventional techniques to obtain a lyophilized material, which is stored (e.g. in a vial in the presence of a suitable gas) and which can be reconstituted with an aqueous carrier to finally give a gas-filled microbubbles suspension where the dimensions and size distribution of the microbubbles are substantially comparable with the dimensions and size distribution of the suspension of microdroplets.

A further process for preparing gas-filled microbubbles comprises generating a gas microbubble dispersion by submitting an aqueous medium comprising a phospholipid (and optionally other amphiphilic film-forming compounds and/or additives) to a controlled high agitation energy (e.g. by means of a rotor stator mixer or by sonication) in the presence of a desired gas and using the obtained mixture as such or subjecting the obtained dispersion to lyophilisation to yield a dried reconstitutable product. An example of this process is given, for instance, in WO97/29782, here enclosed by reference.

Spray drying techniques (as disclosed for instance in U.S. Pat. No. 5,605,673) can also be used to obtain a dried powder, reconstitutable upon contact with physiological aqueous carrier to obtain gas-filled microbubbles.

The precursor in dried or lyophilized form obtained with any of the above techniques will generally be in the form of a powder or a cake, and can be stored (e.g. in a vial) in contact with the desired gas. The precursor is readily reconstitutable, in the presence of the desired gas, in a suitable physiologically acceptable aqueous liquid carrier, which is typically injectable, to form the gas-filled microbubbles, upon gentle agitation of the suspension. Suitable physiologically acceptable liquid carriers are sterile water, aqueous solutions such as saline (which may advantageously be balanced so that the final product for injection is not hypotonic), or solutions of one or more tonicity adjusting substances such as salts or sugars, sugar alcohols, glycols or other non-ionic polyol materials (eg. glucose, sucrose, sorbitol, mannitol, glycerol, polyethylene glycols, propylene glycols and the like).

According to an embodiment of the invention, a targeting construct (i.e. comprising the targeting ligand bound to a component of the microvesicle) can be admixed as such with the other components of the formulation, so to be incorporated into the stabilizing envelope upon reconstitution of the freeze-dried material obtained according to any of the above preparation methods.

Alternatively, the initial formulation of microbubbles may contain suitably intermediate functionalized component (e.g. a maleimide-containing phosphatidylethanolamine), to produce a freeze-dried material containing said intermediate; the targeting ligand, containing a suitable complementary reactive moiety (e.g. thiol), is then linked, by reacting the respective reactive moieties, to the intermediate functionalized compound already incorporated in the envelope of the reconstituted microbubbles.

In the case of the process disclosed in WO2004/069284, the targeting construct comprising the targeting ligand bound to the microvesicle's component can also be admixed with the components of the initial mixture, undergoing to the emulsion and lyophilisation steps. Alternatively, a micellar suspension containing the targeting construct can be separately prepared and subsequently added to the already formed emulsion (containing the other film-forming components), preferably under heating. As above, instead of the formed construct, a functionalized intermediate can alternatively be used, which can then be reacted at any step of the process (e.g. in the emulsion phase or upon reconstitution of the lyophilized compound) with a targeting ligand containing a complementary reactive moiety. According to an embodiment, a functionalized envelope-forming component (or envelope-forming/spacer intermediate construct) is added as a micellar suspension to the formed emulsion, under agitation. The targeting ligand (containing the complementary reactive moiety) is then added to the obtained emulsion.

According to a preferred embodiment the peptide sequence as set forth in SEQ ID NO:3, in dimeric form, is first reacted with a thiolating agent (selected, for instance, among those previously illustrated) to introduce a reactive thiol group on the primary amino group of the C-terminal Lysine residue. The thiolating agent is preferably employed in a molar excess with respect to the Lysine residue, preferably from about 5 to 200 times molar excess, more preferably from 20 to 100 times and even more preferably of about 50 times. The thiolated peptide is then added to a suspension of a maleimide-containing component of gas-filled microvesicles (e.g. a maleimide-modified pegylated phospholipid, such as DSPE-PEG-maleimide). The mixture is then incubated and the obtained construct (comprising SEQ ID NO:3 and the micmrovesicle's component) can be used for the subsequent preparation steps of the gas-filled microvesicles, as above illustrated.

The amount of targeting ligand bound to the surface of a microvesicle is selected so as to preferably provide a multivalent microvesicle, i.e. a microvesicle comprising a plurality of targeting ligand on its surface. In general, the microvesicle comprises at least 200 targeting molecules per $\mu m^2$ of microvesicles surface, preferably at least 500 molecules/$\mu m^2$, more preferably at least 1000 molecules/$\mu m^2$, and even more preferably at least 2000 molecules/$\mu m^2$. On the other side, as a too high concentration of targeting ligand on the surface of the microvesicle is not necessarily required, the microvesicle generally comprises less than 15000 targeting molecules per $\mu m^2$ of microvesicle surface, preferably less than 12000 molecules/$\mu m^2$, more preferably less than 10000 molecules/$\mu m^2$, and even more preferably less than 8000 molecules/$\mu m^2$.

The amount of targeting ligand bound at the surface of a microvesicle can be determined according to common techniques known in the art. For instance, the total surface of the envelope of the microvesicles in a microvesicles suspension can be first determined, e.g. by Coulter Counter measurement. Then, the total amount of molecules of targeting ligand in the microvesicles suspension can be determined, e.g. by measuring the total amount of a chemical marker of the targeting ligand (for instance sialic acid or a specific amino acid), for instance by Liquid-Chromatography Mass Spectrometry (LC-MS). The density of targeting ligand on the microvesicles surface can then be easily calculated.

Use of Targeted Microvesicles

The targeted gas-filled microvesicles of the invention can be used in any in vitro or in vivo analysis requiring the detection of receptors capable of binding to the targeting ligand above identified, such as tissues or cells expressing a selectin receptor, preferably E-selectin and/or P-selectin receptors, more preferably p-selectin receptors. In particular the microvesicles of the invention are useful in diagnostic methods for detecting possible pathological conditions of vascular endothelium, in particular in connection with inflammatory processes (e.g. acute coronary syndrome, angiogenesis, rheumatoid arthritis, Crohn's disease, etc.) and, more in general, of any organ or tissue expressing P-selectin and/or E-selectin. Furthermore, microvesicles according to the invention can be employed as an efficient diagnostic tool during the (therapeutic) treatment of a patient suffering from an inflammatory disease or pathology, where "during" includes any time before the beginning of the treatment, in the course of said treatment and/or at the end of said treatment. For instance the microvesicles of the invention can advantageously be employed in the monitoring and/or follow-up of an anti-inflammatory treatment (e.g. of any of the above cited diseases or pathologies), e.g. to determine or evaluate the effects of the administration of an anti-inflammatory or inflammatory-inhibitor drug on the disease or pathology. In a preferred embodiment, during a treatment a region of interest of the patient is subjected to ultrasound imaging upon administration of the microvesicles of the invention, for instance at regular time intervals, at a predetermined time interval after each drug administration or therapeutic intervention and/or after a selected number of drug administrations or treatments; a final imaging of the region of interest is then preferably performed at the end or conclusion of the treatment.

The gas-filled microvesicles of the invention can further be used in therapeutic-associated imaging methods, said therapeutic-associated imaging including any method for the treatment of a disease in a patient which comprises the use of a contrast imaging agent (e.g. for the delivery of a therapeutic compound to a selected receptor or tissue), and which is capable of exerting or is responsible to exert a biological effect in vitro and/or in vivo. Therapeutic-associated imaging may advantageously be associated with the controlled localized destruction of the gas-filled microvesicles, e.g. by means of ultrasound waves at high acoustic pressure (typically higher than the one generally employed in non-destructive diagnostic imaging methods). This controlled destruction may be used, for instance, for the treatment of blood clots (a technique also known as sonothrombolysis), optionally in combination with the release of a suitable therapeutic compound associated with the contrast agent. Alternatively, said therapeutic-associated imaging may include the delivery of a therapeutic agent into cells, as a result of a transient membrane permeabilization at the cellular level induced by the localized burst or activation of the microvesicles. This technique can be used, for instance, for an effective delivery of genetic material into the cells; alternatively, a drug can be locally delivered, optionally in combination with genetic material, thus allowing a combined pharmaceutical/genetic therapy of the patient (e.g. in case of tumor treatment). The therapeutic agent can be associated with the gas-filled microvesicle according to conventional methods, or can be administered as a separate compound of the composition.

Typically, an effective amount of the contrast agent is administered (e.g. by injection) to a patient in need thereof and the body part or tissue of the patient to be imaged or treated ("region of interest") is subjected to the desired imaging method. Preferably, the contrast agent is administered intravenously. The term patient includes any subject (human or animal) undergoing the administration of the contrast agent, either for diagnostic/therapeutic purposes or for experimental purposes (including, for instance, use of a contrast agent in laboratory animals, e.g. to follow an experimental therapeutic treatment).

According to a preferred embodiment, an effective amount of targeted microvesicles is administered to a patient, typically by injection of a suspension thereof. The imaging of the region of interest will thus be enhanced by the presence of the microvesicles bound to the receptor in the region of interest.

A variety of imaging techniques may be employed in ultrasound applications, for example including fundamental and non-linear (e.g. harmonic) B-mode imaging, pulse or phase inversion imaging and fundamental and non-linear Doppler imaging; if desired three- or four-dimensional imaging techniques may be used. Furthermore, diagnostic techniques entailing the destruction of gas-filled microvesicles (e.g. by means of ultrasound waves at high acoustical pressure) which are highly sensitive detection methods are also contemplated.

Microvesicles according to the invention can typically be administered in a concentration of from about 0.01 to about 5.0 µl of gas (entrapped inside the microvesicles) per kg of patient, depending e.g. on their respective composition, the tissue or organ to be imaged and/or the chosen imaging technique. This general concentration range can of course vary depending from specific imaging applications, e.g. when signals can be observed at very low doses such as in color Doppler or power pulse inversion. Possible other diagnostic imaging applications include scintigraphy, optical imaging, photo-acoustic imaging, magnetic resonance imaging and X-ray imaging, including X-ray phase contrast imaging.

The following examples will help to further illustrate the invention.

EXAMPLES

The following materials and abbreviations have been used in the following examples.

DSPC Distearoylphosphatidylcholine (Genzyme)
Palmitic acid Palmitic acid, Hexadecanoic acid (Fluka)
DSPE-PEG2000 Distearoylphosphatidylethanolamine modified with PEG2000, sodium salt (Genzyme)
DSPE-PEG2000-mal Distearoylphosphatidylethanolamine modified with PEG2000-maleimide (Avanti Polar lipids)
DSPE-PEG2000-PDP 1,2 Distearoyl-sn-glycero-3-phosphoethanolamine-N-[3-(2-pyridyldithio)propionate (polyethylene glycol)-2000] ammonium salt (Avant Polar Lipids)
PDP Pyridyldithiopropionyl
Traut reagent 2-Iminothiolane hydrochloride (Pierce)
SATA N-Succinimidyl S-Acetylthioacetate (Pierce)
Sulfo-SMCC (sulfosuccinimidyl 4-[N-maleimidomethyl]cyclohexane-1-carboxylate) (Pierce)
Hydroxylamine.HCl Hydroxylamine hydrochloride (Fluka)
EDTA.4Na Ethylenediamine tetraacetic acid, tetra sodium salt (Fluka)
PEG4000 Polyglycol 4000S from Clariant
Cyclooctane Fluka
TCEP Tris(2-carboxyethyl)-phosphine hydrochloride (Pierce)
rPSGL-Ig Glycosylated SEQ ID NO: 4, obtained according to US 2003/0166521, Example 1
Lys-C Endoprotease Lys-C (Pierce, #90051)
Fr-1 Purified fragment of rPSGL-Ig (SEQ ID NO:3)

Example 1

Enzymatic Digestion of rPSGL-Ig for the Preparation of Fr-1

2 mg of rPSGL-Ig in 200 µL of digestion buffer (Tris.HCl 25 mM—EDTA 1 mM—pH 8.5) were placed in a microcentrifuge tube, to which a solution of Lys-C (40 µg dissolved in 50 µL of distilled water) was added. The vial containing the powder was rinsed with 50 µL of distilled water and added to the microcentrifuge tube. Then, the mixture was incubated 18 h at 37° C. in the Dry Block Heater.

Example 2

Separation of Fr-1 Anion Exchange Chromatography

A chromatographic separation column (Econo-column from Bio-Rad, Vt=3.6 mL, height 9.4 cm) was filled with ANX Sepharose gel (GE Healthcare) and equilibrated in a buffer containing sodium acetate 0.05 M—NaCl 0.05 M (pH 4.0). The column was run with 3-4 volumes of the starting buffer, to allow the gel to settle. The flow rate was approximately 0.23 mL/min.

290 µL of the suspension containing the digested protein obtained in Example 1 were diluted with 440 µL of acetate 0.05 M—NaCl 0.05 M—pH 4.0 buffer. This mixture was applied to the column and the column was eluted with acetate 0.05 M/NaCl buffers pH=4.0 at increasing NaCl concentrations ranging from 0.05 to 1 M.

2 mL fractions were collected during elution. Protein content in each fraction was assessed by a OD (Optical Density) measurement at 280 nm (OD280), and presence of sugar residues were determined by the resorcinol titration. Fr-1 was recovered in fractions eluting at 1 M NaCl concentration. The fractions containing Fr-1 were collected and used for subsequent preparations. Purity of the Fr-1-containing fractions was assessed by SDS-PAGE analysis and LC-UV. The mean molecular weight of Fr-1 (about 32 kDaltons) was determined by MALDI-ToF (Matrix-assisted laser desorption/ionization—time-of-fly).

Example 3

Thiolation of rPSGL-Ig (Comparative)

An aliquot of rPSGL-Ig stock solution (789 µL—15.1 mg of rPSGL-Ig—188.75 nmoles) was diluted with 200 µL of PBE (Phosphate buffer 25 mM, 150 mM saline, 1 mM EDTA, pH 8).

A solution of Traut reagent (2.76 mg/mL—20 mM) was prepared in PBE and 75 µL of this solution were added to the rPSGL-Ig solution. The resulting mixture was incubated at room temperature for 1 h under stirring. This solution was spun through a spin-column (Zeba spin column 5 mL, Pierce, #89891) equilibrated in phosphate buffer 20 mM pH 6. The final volume of the solution was of about 1.2 mL (thiolated rPSGL-Ig concentration: approx. 111 nmoles/mL).

The rPSGL-Ig content in the final solution was determined by UV spectrometry at 280 nm.

The thiolated rPSGL-Ig was used immediately after purification to limit the possible oxidation of thiol groups.

Example 4

Preparation of Microvesicles with rPSGL-Ig Ligand (Comparative)

DSPE-PEG-maleimide (6.6 mg—2.24 μmoles) was dissolved in phosphate buffer 20 mM pH 6 (0.5 mL) at 45° C. with stirring (vortex) to obtain a clear solution. 0.5 mL of the resulting solution were then added to 59.5 mL of a PEG4000 10% solution.

60 mg of a mixture of DSPC/Palmitic acid (80/20 by moles) were dissolved in cyclooctane (4.8 mL) at 70° C.

The above prepared aqueous and organic solutions were admixed by using a high speed homogenizer (Megatron MT3000) for 5 min (11'500 rpm), to obtain an emulsion. The resulting emulsion was heated under stirring at 60° C. for 1 h, then cooled at room temperature (about 22° C.). The emulsion was divided in 10 mL fractions in polypropylene tubes (Falcon-15 mL).

Thiolated rPSGL-Ig prepared according to example 3 (15 nmoles) was added to 10 mL of the emulsion and the resulting mixture was agitated at 22° C. for 2 h 30 min. The obtained emulsion was finally diluted twice with 10 mL of 10% PEG4000 solution and sampled in DIN4R vials (300 μL per vial). Vials were frozen at −50° C. for 2 h (Christ Epsilon lyophilizer), then freeze-dried at −25° C. and 0.2 mbar for 12 h. The lyophilized product was then exposed to an atmosphere containing perfluoro-n-butane and air (35/65 v/v) and the vials were sealed.

The product was dispersed in a volume of saline (1 mL, 150 mM NaCl) by gentle hand shaking before use.

Example 5

Thiolation of Fr-1

Dried Fr-1 (17.1 nmoles) from example 2 was dissolved in 160 μL of PBE (Phosphate buffer 25 mM, 150 mM saline, 1 mM EDTA, pH 8). A solution of SATA 10 mg/mL was prepared in anhydrous DMSO and 4 μL (10 equivalents of SATA) of this solution was added in the Fr-1 solution. The obtained solution was incubated for 30 min at room temperature. The solution was then diluted with PBE (150 μL). This solution was spun through a spin-column (Zeba spin column 2 mL, Pierce, #89890) equilibrated in PBE (using 50 μL of PBE as stacker). The final volume of the solution was of about 360 μL.

A solution of hydroxylamine hydrochloride (0.696 g) and EDTA.tetrasodium salt (0.19 g) was prepared in PBE (15 mL). The pH of this solution was adjusted to 7.3 with NaOH 10 N and the volume was completed to 20 mL. A aliquot of this deacetylation solution (40 μL) was added to the Fr-1 solution (360 μL). The obtained solution was incubated for 2 h at room temperature. This solution was spun through a spin-column (Zeba spin column 2 mL, Pierce, #89890) equilibrated in phosphate buffer 20 mM pH 6 (using 50 μL of PBE as stacker). The final volume of the solution was of about 450 μL (thiolated Fr-1 concentration: approx. 33 nmoles/mL).

The thiolated Fr-1 was used immediately after purification to limit the possible oxidation of thiol groups.

Example 6

Preparation of Microvesicles with Fr-1

DSPE-PEG-maleimide (6.6 mg-2.24 μmoles) was dissolved in phosphate buffer 20 mM pH 6 (0.5 mL) at 45° C. with stirring (vortex) to obtain a clear solution. 0.5 mL of the resulting solution were then added to 59.5 mL of PEG4000 10% solution.

60 mg of a mixture of DSPC/Palmitic acid (80/20 by moles) were dissolved in cyclooctane (4.8 mL) at 70° C.

The above prepared aqueous and organic solutions were admixed by using a high speed homogenizer (Megatron MT3000) for 5 min (11'500 rpm), to obtain an emulsion. The resulting emulsion was heated under stirring at 60° C. for 1 h, then cooled at room temperature (about 22° C.). The emulsion was divided in 10 mL fractions in PP tubes (Falcon-15 mL).

Fr-1 (prepared according example 5, 13 nmoles) was added to 10 mL of the emulsion and the resulting mixture was gently stirred at 22° C. for 2 h 30 min. The obtained emulsion was finally diluted twice with 10% PEG4000 solution and sampled in DIN4R vials (300 μL per vial). Vials were frozen at −50° C. for 2 h (Christ Epsilon lyophilizer), then freeze-dried at −25° C. and 0.2 mbar for 12 h. The lyophilized product was then exposed to an atmosphere containing perfluoro-n-butane and air (35/65 v/v) and the vials were sealed.

The product was dispersed in a volume of saline (1 mL, 150 mM NaCl) by gentle hand shaking before use.

Example 7

Reduction of Fr-1 with TCEP: Monomeric Fr-1

Dried Fr-1 (fragmented and purified from 3 mg of rPSGL-Ig according example 1 and example 2) was dissolved in 250 μL of buffer (Tris/HCl 50 mM, 50 mM EDTA, pH 6.8).

A solution of TCEP (2.86 mg/mL—10 mM) was prepared in the same buffer and 28 μL of this solution were added to the fragment solution. The resulting mixture was incubated at 37° C. for 1 h under stirring. After dilution with 100 μL of buffer, this solution was spun through a spin-column (Zeba spin column 2 mL, Pierce) equilibrated in Phosphate buffer 20 mM pH 6. The final volume of the solution was about 0.4 mL.

A reduced monomeric Fr-1 was obtained and this compound was immediately used after purification (to limit the possible reoxidation of thiol groups).

Example 8

Preparation of Microvesicles with Monomeric Fr-1 (After TCEP Reduction)

Microvesicles were prepared according example 6, with the difference that the Fr-1 solution was replaced by a solution of monomeric Fr-1 (100 nmol) prepared according to example 7.

Example 9

Preparation of Fr1-SMCC

Fr-1 (76.5 nmoles) from example 2 was dissolved in 500 μL of buffer (Phosphate buffer 200 mM, 50 mM saline, 1 mM EDTA, pH 7.5). A solution of Sulfo-SMCC 55 mg/mL was prepared in anhydrous DMSO and 62 μL (100 equivalents of Sulfo-SMCC) of this solution was added to the Fr-1 solution. The solution was incubated at room temperature for 45 min. This solution was spun through a spin-column (Zeba spin column 5 mL, Pierce, #89890) equilibrated in Phosphate buffer 20 mM pH 6. The final volume of the solution was of about 660 μL.

Example 10

Preparation of DSPE-PEG-SH

DSPE-PEG2000-PDP (4.4 mg—1473 nmoles) was dissolved in 400 µL of Phosphate buffer (100 mM pH 6) at 40° C. with stirring (vortex) to obtain a clear solution. A 25 mM solution of TCEP in buffer (125 µL) was added. The obtained solution was incubated for 45 min at room temperature with stirring.

A sample of the solution was diluted in buffer and checked for the absence of 2-pyridine thione.

The solution was spun through a spin-column (Zeba spin column 5 mL, Pierce, #89890) equilibrated in Phosphate buffer 20 mM pH 6. The final volume of the solution was of about 620 µL.

Example 11

Preparation of DSPE-PEG-SH/Fr-1-SMCC Conjugate

630 µL of Fr1-SMCC solution (70 nmoles) obtained in example 9 was added in 470 µL of DSPE-PEG-SH solution (1050 nmoles) obtained in example 10. The solution was incubated for three hours at room temperature with stirring (rotating wheel).

The solution was then purified by anion exchange chromatography with an ANX Sepharose gel (GE Healthcare).

The solution containing the purified Fr-1 conjugate (2.6 mL) was spun through a spin-column (Zeba spin column 10 mL, Pierce, #89893) equilibrated in Phosphate buffer 20 mM pH 6 and used for subsequent preparations.

Example 12

Preparation of Microvesicles with DSPE-PEG-SH/Fr-1-SMCC Conjugate 10 mg of a mixture of DSPC and Palmitic acid (80/20 by moles) were dissolved in cyclooctane (0.8 mL) at 70° C.

Separately, the DSPE-PEG-SH/Fr-1-SMCC conjugate solution prepared according to example 11 (0.75 mL—20 nmoles) was added to 9.25 mL of PEG4000 10% solution.

The above prepared organic and aqueous solutions were admixed by using a high speed homogenizer (Polytron PT3000) for 1 min (8'000 rpm), to obtain an emulsion. The resulting emulsion was heated under stirring at 60° C. for 1 h, then cooled at room temperature (about 22° C.).

The obtained emulsion was diluted twice with 10% PEG4000 solution and sampled in DIN4R vials (300 µL per vial). Vials were frozen at −50° C. for 2 h (Christ Epsilon lyophilizer), then freeze-dried at −25° C. and 0.2 mbar for 12 h. The lyophilized product was then exposed to an atmosphere containing perfluoro-n-butane and air (35/65 v/v) and the vials were sealed.

The product was dispersed in a volume of saline (1 mL, 150 mM NaCl) by gentle hand shaking.

Example 13

Preparation of Microvesicles with DSPE-PEG-SH/Fr-1-SMCC Conjugate 10 mg of a mixture of DSPC and Palmitic acid (80/20 by moles) were dispersed in distilled water (10 mL) at 70° C. for 15 min and then cooled to room temperature; the DSPE-PEG-SH/Fr-1-SMCC conjugate solution prepared according to example 11 (20 nmoles) was then added to the dispersion under stirring.

Cyclooctane (0.8 mL) was admixed with the obtained dispersion by using a high speed homogenizer (Polytron PT3000) for 1 min (8'000 rpm). The resulting emulsion was heated under stirring at 60° C. for 1 h, then cooled at room temperature (about 22° C.).

The emulsion was diluted twice with 20% PEG4000 solution and sampled in DIN4R vials (300 µL per vial). Vials were frozen at −50° C. for 2 h (Christ Epsilon lyophilizer), then freeze-dried at −25° C. and 0.2 mbar for 12 h. The lyophilized product was then exposed to an atmosphere containing perfluoro-n-butane and air (35/65 v/v) and the vials were sealed.

The product was dispersed in a volume of saline (1 mL, 150 mM NaCl) by gentle hand shaking.

Example 14

Preparation of Microvesicles with rPSGL-Ig Ligand (Comparative)

DSPE-PEG-mal (0.44 mg—0.15 µmole) was dissolved in phosphate buffer 20 mM pH 6 (0.1 mL) at 45° C. with stirring (vortex) to obtain a clear solution. Thiolated rPSGL-Ig prepared according example 3 (16 nmoles—144 µL—0.8 nmoles/mL emulsion) was added to the solution and the resulting mixture was agitated at 22° C. for 2 h 30 min. 0.25 mL of the solution were then added to 19.75 mL of PEG4000 10% solution.

20 mg of a mixture of DSPC/Palmitic acid (80/20 by moles) were dissolved in cyclooctane (1.6 mL) at 70° C.

The above prepared aqueous and organic solutions were admixed by using a high speed homogenizer (Polytron PT3000) for 1 min (11'000 rpm), to obtain an emulsion. The resulting emulsion was heated under stirring at 60° C. for 1 h, then cooled at room temperature (about 22° C.).

The obtained emulsion was finally diluted twice with 10% PEG4000 solution and sampled in DIN4R vials (300 µL per vial). Vials were frozen at −50° C. for 2 h (Christ Epsilon lyophilizer), then freeze-dried at −25° C. and 0.2 mbar for 12 h. The lyophilized product was then exposed to an atmosphere containing perfluoro-n-butane and air (35/65 v/v) and the vials were sealed.

Example 15

Preparation of Microvesicles with Fr-1

Microvesicles were prepared according to example 14 except that thiolated rPSGL-Ig was replaced by thiolated Fr-1 (25 nmoles, prepared according example 5).

Example 16

Physico-Chemical Characterization After Dispersion of Ligand-Containing Microvesicles The freeze-dried product obtained in comparative example 14 was dispersed by gentle shaking in a volume of saline (1 mL, 150 mM NaCl), in order to obtain an isotonic microvesicles suspension ready for intravenous injection. The microvesicles suspension was subjected to size analysis immediately after preparation of the suspension (Time=0 min), and 30 min after preparation (Time=30 min). The size distribution and concentration of microvesicles were measured with a Multisizer™ 3 Coulter Counter® fitted with a 30 µm aperture tube (Dilution: 50 µL of microvesicles suspension in 100 mL NaCl 0.9% solution—Analytical volume: 100 µL). The preparation was characterized to determine the mean diameter in number and median diameter in volume of microvesicles (Dn and Dv50 in µm), as well as their concentration in number, were obtained.

Similarly, also the freeze-dried product obtained in example 15 was dispersed in an equal volume of saline and the size and distribution of the microvesicles in the suspension were determined as above indicated (Time=0 or 30 min).

Results are provided in the following table 1.

TABLE 1

Physico-chemical characterization of microvesicles suspensions

| Example | Time [min] | Diameter Dv50 [µm] | Diameter Dn [µm] | Microvesicle conc. [×10$^8$/mL] |
|---|---|---|---|---|
| 14 (comp) | 0 | 3.0 | 1.5 | 11.5 |
| 14 (comp) | 30 | 2.5 | 1.3 | 18.3 |
| 15 | 0 | 2.7 | 1.3 | 16.8 |
| 15 | 30 | 2.6 | 1.3 | 15.8 |

As inferable from the above results, microvesicles with rPSGL-Ig ligand suffered from aggregation after dispersion in saline, gradually disaggregating over time, which is not desirable for an injectable form. On the contrary, the size, distribution and vesicles count for the Fr-1 containing microvesicles were substantially constant when compared at T=0 min and at T=30 min after dispersion.

Example 17

Image Analysis of Microvesicles Suspensions After Reconstitution in 0.9% NaCl.

Microvesicles suspensions obtained according to example 14 and example 15 were diluted 1/10 in 0.9% NaCl and a 10 µL aliquotes were introduced into a Neubauer counting cell (Blaubrand®, Brand GmbH), under an optical microscope (Leica Cambridge Ltd, fitted with a 20× objective lens), for microvesicles image acquisition. The microvesicles were allowed to rise to the cover slip at the top of the Neubauer cell (2 to 3 min) and after focusing, images were taken with the digital camera. The images were then analysed with a mathematical processor, to determine the amount of unbound microvesicles, based on the assumption that a pure circular shape in the image corresponds to a single non-aggregated microvesicle, while aggregations of microvesicles produce undetected non-circular shapes. To detect "pure circular shapes" in the grayscale images, the circular Hough transform was implemented in Matlab (The Mathworks Inc., Natick, Mass.). The program outputs the center positions and radii of the detected circular shapes. The following results (Table 2) were observed.

TABLE 2

Image analysis by Hough transform object detection

| | Number of non-aggregated microvesicles | | |
|---|---|---|---|
| Preparation | Vial #1 | Vial #2 | Vial #3 |
| Example 14 | 157 | 131 | 172 |
| Example 15 | 332 | 354 | 352 |

As inferable from the results in Table 2, microvesicles containing the Fr-1 fragment are much less prone to aggregation than microvesicles containing the entire protein rPSGL-Ig.

Example 18

In vitro Binding Activity of Targeted Microvesicles

To test the effective binding, targeted microvesicles prepared according to comparative example 4 were injected in a flow chamber set up comprising a coating of mouse Fc P-Selectin (CD62P-Fc Chimera, from R&D Systems (Minneapolis, Minn., USA). Microvesicles (at equivalent number of 80×10$^6$/400 µL TBS++) were injected through the flow chamber (FCS2, Bioptech, USA) in a bolus fashion and their adhesion onto the mouse P-selectin coating layer was assessed over a period of 10 min at a flow rate of 1.0 mL/min (shear rate of 714 s$^{-1}$) in the presence of 50% human plasma in PBS (v:v, Biomeda collected on citrate, ref. ES1020P, Stehelin & Cie AG). A quantitative analysis of microvesicles accumulation was performed by counting the number of microvesicles adhering in the observed area at 2 min intervals over the total 10 min infusion, using the image processing program Analysis FIVE (SIS, Germany). After 10 min, five pictures were taken randomly and the number of bound microvesicles was measured and expressed as the number of bound bubbles at 10 min (NBB). Each observed area was 183×137 µm, as measured with the aid of a stage micrometer. Measurement was performed between the middle and the exit of the chamber.

Similarly, suspensions of targeted microvesicles prepared according to example 6 (Fr-1 targeting ligand) and according to example 8 (monomeric FR-1) were injected in a flow chamber as described above, and their binding activity determined according to the above procedure.

Table 3 shows the results of the three tests.

TABLE 3

| Number of bound microveicles at 10 min (NBM 10 min) | |
|---|---|
| Preparation | NBM 10 min |
| Example 4 | 75 ± 8 |
| Example 6 | 98 ± 7 |
| Example 8 | 88 ± 9 |

As inferable from the above results, the binding activity of microvesicles containing Fr-1 is higher with respect to corresponding preparations of microvesicles containing monomeric Fr-1 or the complete protein rPSGL-Ig.

Example 19

In Vivo Performance of Microvesicles with Dimeric and Monomeric Fr-1

Microvesicles prepared according to examples 6 and 8, were compared in an inflammatory rat model. Inflammation was induced in the hind limb by an intramuscular injection of lipopolysaccharide (LPS, 026:B6 Sigma L-8274, 2.1 mg/kg). The effective binding of the targeted microvesicles was evaluated by ultrasound imaging 24 h after induction of the inflammatory process. Ultrasound imaging was performed using a Siemens Sequoia 512 scanner (Siemens Medical Systems, Issaquah, Wash.) equipped with a 15L8 linear transducer (transmit frequency, 7 MHz; dynamic range, 83 dB; depth, 20 mm; Time-Gain compensation (TGC): linear). 10 min after single dose injections of microvesicles obtained from example 6 and from example 8, a quantitative analysis of microvesicles binding was performed using a quantification software developed in-house (Bracco Suisse SA, Geneva, Switzerland) designed to quantify contrast echo-power amplitude within areas of interest (AOI). Contrast enhancement in the AOI of the stored frames was expressed as relative echo-power values (rms$^2$), which are proportional to the number of microvesicles in the selected AOI. Results are shown in table 4.

TABLE 4

| Echo power in inflamed rat muscle | |
|---|---|
| Preparation | Echo power 10 mm ($rms^2$) |
| Example 6 | 43 ± 18 |
| Example 8 | 18 ± 10 |

As inferable from the above table, the microvesicles of example 6 (with dimeric Fr-1) result in a higher in-vivo binding with respect to the microvesicles of example 8 (with monomeric Fr-1).

Example 20

Monitoring the Effects of Anti-Inflammatory Therapy with Fr-1 Microvesicles

Microvesicles prepared according to example 6 were administered in an inflammatory rat model. Inflammation was induced in the hind limb by an intramuscular injection of lipopolysaccharide (LPS, 026:B6 Sigma L-8274, 2.1 mg/kg). Monitoring of anti-inflammatory treatment efficacy was performed by pre-treating animals twenty four hours before LPS administration, with a sub-cutaneous injection of etanercept (0.45 mg/kg, Wyeth) or of saline. The in vivo binding activity of Fr-1 microvesicles was determined according to the imaging protocol described in example 19. The known inhibition of inflammation achieved by administration of etanercept to prevent TNFα activity (Campbell, S. J., Jiang, Y., Davis, A. E., Farrands, R., Holbrook, J., Leppert, D., and Anthony, D. C. (2007), Immunomodulatory effects of etanercept in a model of brain injury act through attenuation of the acute-phase response. J. Neurochem. 103, 2245-2255) was visualized using Fr-1 microvesicles. Animals pre-treated with etanercept, showed a decrease in Fr-1 microvesicles accumulation, in comparison to control animals receiving saline. This study shows the ability of Fr-1 microvesicles to monitor expression of selectin receptors in an inflammation site during an anti-inflammatory treatment with an inflammation inhibitor.

The invention claimed is:

1. A targeting construct comprising:
   a) an amphiphilic compound; and
   b) a homodimeric polypeptide consisting of two polypeptide monomers, wherein each polypetide monomer consists of at most 200 amino acid residues, comprises a single lysine amino acid residue, at least amino acids 5-16 as set forth in SEQ ID NO:1 and at least one cysteine residue;
   wherein the peptide monomers form a disulfide bond with the respective cysteine residues;
   said homodimeric polypeptide being covalently associated with said amphiphilic compound.

2. The targeting construct according to claim 1 wherein said polypeptide monomers comprise at least amino acids 1-19 as set forth in SEQ ID NO: 1.

3. The targeting construct according to claim 1 wherein said polypeptide monomers comprise at least amino acids 5-41 as set forth in SEQ ID NO: 1.

4. The targeting construct according to claim 1 wherein said polypeptide monomers comprise at least amino acids 1-47 as set forth in SEQ ID NO: 1.

5. The targeting construct according to claim 1 wherein said polypeptide monomers comprise at most 100 amino acid residues.

6. The targeting construct according to claim 1 wherein said polypeptide monomers comprise at most 75 amino acid residues.

7. The targeting construct according to claim 1 wherein said polypeptide monomers consist of the amino acid sequence as set forth in SEQ ID NO: 3.

8. The targeting construct according to claim 1 wherein said polypeptide monomers consist of the amino acid sequence of formula (I):

$(X^A)_n—Y—(X^B)_m$     (I)

where:
$(X^A)_n$ represents a sequence of n amino acids $X^A$ where:
  n is an integer of from 12 to 199;
  $X^A$ is any amino acid with the exclusion of lysine; and
  $(X^A)_n$ further comprises at least amino acids 5-16 as set forth in SEQ NO:1 and at least one cysteine;
$(X^B)_m$ represents a sequence of m amino acids $X^B$, where:
  m is an integer from 0 to 10, with the proviso that the sum m+n is at most 199; and
  $X^B$ is any amino acid with the exclusion of lysine and cysteine; and
Y is lysine.

9. The targeting construct according to claim 8 wherein $(X^A)_n$ comprises at least amino acids 1-19 as set forth in SEQ ID NO:1.

10. The targeting construct according to claim 8 wherein $(X^A)_n$ comprises at least amino acids 5-41 as set forth in SEQ ID NO:1.

11. The targeting construct according to claim 8 wherein $(X^A)_n$ comprises at least amino acids 1-47 as set forth in SEQ ID NO:1.

12. The targeting construct according to claim 8 wherein n is an integer of from 12 to 99 and m+n is at most 99.

13. The targeting construct according to claim 8 wherein n is an integer of from 12 to 74 and m+n is at most 74.

14. The targeting construct according to claim 8 wherein $X^A$ comprises two cysteine residues.

15. The targeting construct according to claim 1 wherein said polypeptide monomers are glycosylated comprising an O-glycan moiety.

16. The targeting construct according to claim 15 wherein said O-glycan moiety comprises a sialyl Lewis x structure.

17. The targeting construct according to claim 15 comprising one or more glycan residues bound to amino acids in positions 16, 24, 25, 26, 28, 29, 32, 36, 39, 40 and/or 41 of SEQ ID NO:1.

18. The targeting construct according to claim 4 wherein said polypeptide monomers are glycosylated comprising an O-glycan moiety.

19. The targeting construct according to claim 18 wherein said O-glycan moiety comprises a sialyl Lewis x structure.

20. The targeting construct according to claim 18 comprising one or more glycan residues bound to amino acids in positions 16, 24, 25, 26, 28, 29, 32, 36, 39, 40 and/or 41 of SEQ ID NO:1.

21. The targeting construct according to claim 8 wherein said polypeptide monomers are glycosylated comprising an O-glycan moiety.

22. The targeting construct according to claim 21 wherein said O-glycan moiety comprises a sialyl Lewis x structure.

23. The targeting construct according to claim 21 comprising one or more glycan residues bound to amino acids in positions 16, 24, 25, 26, 28, 29, 32, 36, 39, 40 and/or 41 of SEQ ID NO:1.

24. The targeting construct according to claim 1 wherein said polypeptide monomers further comprise a sulfate group bound to a tyrosine.

25. The targeting construct according to claim 4 wherein said polypeptide monomers further comprise a sulfate group bound to a tyrosine.

26. The targeting construct according to claim 1 wherein said amphiphilic compound is a phospholipid.

27. The targeting construct according to claim 4 wherein said amphiphilic compound is a phospholipid.

* * * * *